(12) United States Patent
Xin et al.

(10) Patent No.: US 9,593,290 B2
(45) Date of Patent: *Mar. 14, 2017

(54) LUBRICATING OIL COMPOSITION AND PRODUCTION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Shihao Xin, Beijing (CN); Xin Xie, Beijing (CN); Zuoxin Huang, Beijing (CN); Qinghua Duan, Beijing (CN); Zhiqiang Wu, Beijing (CN); Lihua Wang, Beijing (CN)

(73) Assignees: CHINA PETROLEUM & CHEMICAL CORPORATION, Beijing (CN); RESEARCH INSTITUTE OF PETROLEUM PROCESSING SINOPEC, Beijing (CN)

( * ) Notice: Subject to any disclaimer, the term of this patent is extended or adjusted under 35 U.S.C. 154(b) by 85 days.

This patent is subject to a terminal disclaimer.

(21) Appl. No.: 14/397,355

(22) PCT Filed: Apr. 25, 2013

(86) PCT No.: PCT/CN2013/000474
§ 371 (c)(1),
(2) Date: Oct. 27, 2014

(87) PCT Pub. No.: WO2013/159571
PCT Pub. Date: Oct. 31, 2013

(65) Prior Publication Data
US 2015/0126420 A1  May 7, 2015

(30) Foreign Application Priority Data

Apr. 26, 2012 (CN) .......................... 2012 1 0127904

(51) Int. Cl.
*C10M 133/54* (2006.01)
*C10M 159/16* (2006.01)
(Continued)

(52) U.S. Cl.
CPC ......... *C10M 133/54* (2013.01); *C07C 215/50* (2013.01); *C08F 110/10* (2013.01);
(Continued)

(58) Field of Classification Search
CPC .............. C10M 133/54; C10M 159/16; C10M 2215/26; C10M 2217/043; C10L 1/2366;
(Continued)

(56) References Cited

U.S. PATENT DOCUMENTS 4,242,212 A    12/1980 Hanson
5,608,029 A *   3/1997 Thaler .................. C07D 233/02
                                                          508/558
(Continued)

FOREIGN PATENT DOCUMENTS

CN    1541200 A    10/2004
CN    1720317 A     1/2006
(Continued)

OTHER PUBLICATIONS

International Search Report dated Aug. 1, 2013 issued in International Application No. PCT/CN2013/000474.
(Continued)

*Primary Examiner* — James Goloboy
(74) *Attorney, Agent, or Firm* — Scully Scott Murphy & Presser

(57) ABSTRACT

This invention relates to a lubricating oil composition and production thereof. The lubricating oil composition com-
(Continued)

prises a Mannich base represented by the following formula (III) (wherein A and $R_2$ are as defined in the specification) and a lubricant base oil. The lubricating oil composition according to this invention exhibits excellent cleansing and dispersing performance and excellent anticorrosion performance.

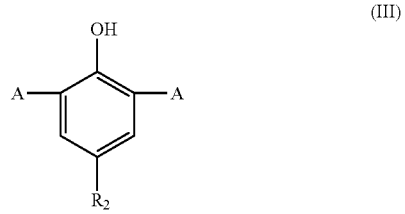

(III)

14 Claims, 4 Drawing Sheets

(51) Int. Cl.
*C07C 215/50* (2006.01)
*C10L 1/238* (2006.01)
*C10L 10/04* (2006.01)
*C11D 3/37* (2006.01)
*C11D 3/30* (2006.01)
*C08F 110/10* (2006.01)
*C10L 1/236* (2006.01)

(52) U.S. Cl.
CPC ............ *C10L 1/238* (2013.01); *C10L 1/2366* (2013.01); *C10L 10/04* (2013.01); *C10M 159/16* (2013.01); *C11D 3/30* (2013.01); *C11D 3/3723* (2013.01); *C10L 2200/0423* (2013.01); *C10L 2200/0446* (2013.01); *C10L 2250/04* (2013.01); *C10M 2215/26* (2013.01); *C10M 2217/043* (2013.01); *C10N 2230/04* (2013.01)

(58) Field of Classification Search
CPC .. C10L 1/238; C10L 10/04; C10L 2200/0423; C10L 2200/0446; C10L 2250/04; C11D 3/30; C11D 3/3723; C10N 2230/04; C07C 215/50; C08F 110/10
USPC .................................................. 508/370, 542
See application file for complete search history.

(56) References Cited

U.S. PATENT DOCUMENTS

| | | | |
|---|---|---|---|
| 5,652,201 A * | 7/1997 | Papay | C10M 159/12 508/228 |
| 5,725,612 A | 3/1998 | Malfer et al. | |
| 2004/0168364 A1* | 9/2004 | Macduff | C08F 8/32 44/415 |
| 2008/0141583 A1 | 6/2008 | Malfer et al. | |
| 2009/0094887 A1 | 4/2009 | Calvert et al. | |

FOREIGN PATENT DOCUMENTS

| | | |
|---|---|---|
| CN | 101058761 A | 10/2007 |
| CN | 101067097 A | 11/2007 |
| CN | 101126039 A | 2/2008 |
| CN | 102516097 A | 6/2012 |
| EP | 1 375 629 A2 | 1/2004 |
| EP | 1 712 605 A1 | 10/2006 |

OTHER PUBLICATIONS

European Search Report dated Apr. 4, 2016 issued in EP Patent Appln. No. 13781793.8, corresponding to PCT/CN2013000473.

* cited by examiner

LUBRICATING OIL COMPOSITION AND PRODUCTION THEREOF

TECHNICAL FIELD

This invention relates to a lubricating oil composition, especially relates to a lubricating oil composition exhibiting excellent cleansing and dispersing performance and excellent anticorrosion performance. This invention further relates to a process for producing the lubricating oil composition.

BACKGROUND ART

Unsaturated olefins, aromatics, and minor amounts of sulfur-containing compounds in a lubricant base oil tend to form gums by reacting with oxygen, and finally to form carbon deposits, especially at critical locations like inlet valves, pistons, oil pans and the combustion chamber, which will facilitate formation of engine deposits and seriously affect the performance of the engine, causing engine problems like difficult starting, idle instability, poor driving, poor acceleration, and severe power loss. Carbon deposits hinder the rotation of transmission gears, worsen gear wear and shorten the gearbox life, resulting in unnecessary expensive maintenance cost. By adding a cleansing and dispersing agent to a lubricant base oil as the lubricating oil additive, the prior art has developed a lubricating oil composition exhibiting cleansing performance (i.e. deposit formation suppressing performance). With this lubricating oil composition having cleansing performance, coking and carbon depositing on the top of pistons can be effectively reduced, which helps to reduce valve system, engine parts and gear wear, and finally elongate the safe operation cycle of engines and gears and the service life of spare parts.

U.S. Pat. No. 5,725,612 discloses a Mannich base and a process for producing same. The Mannich base is produced by reacting a hydrocarbyl-substituted alkyl o-cresol with an aldehyde and an amine, and after produced into a cleansing agent, exhibits some deposit formation suppressing performance.

US 20040168364 discloses a Mannich base and a process for producing same. The Mannich base is produced by the reaction of a phenolic compound with an aldehyde and an amine, and after produced into a cleansing agent, exhibits some deposit formation suppressing performance.

In recent years, the product specification of gasoline engine oils has been gradually upgraded from SJ/GF-2 to SL/GF-3, SM/GF-4 and SN/GF-5. The dispersing and cleansing performance of engine oils has been always identified as one of the critical indexes of the product specification. According to the recent SN/GF-5 specification in 2010, more stringent requirements have been raised on the piston cleansing ability of engine oils in the IIIG engine test, with the pass criteria in a piston deposit rating upgraded from 3.5 to 4, which represents a significant increase. Further, more stringent requirements have been raised on the engine sludge rating in the VG engine test evaluation, with less amount of sludge under more severe working conditions. All of these laid more and more stringent requirements on the cleansing and dispersing agent in lubricating oils. In addition, the product specification and grade of diesel engine oils have been changing as the diesel engine structure or operating conditions change, and further in response to the energy-saving and emission-reduction requirement, resulting in frequently upgrading of diesel engine oils. The product specification of diesel engine oils has been gradually upgraded from CF-4 to CH-4, CI-4 and most recently CJ-4. The application of the EGR exhaust gas recirculation system to the diesel engine decreases NOx emission, however, brings about the problem of increasing soot in lubricating oils. In use, carbon black in the diesel engine oil has been increased from a content of 2% according to the CF-4 specification gradually to 6.7% according to the CJ-4 specification. This will raise more and more stringent requirements on the piston cleansing performance and the soot dispersing performance of oil products.

However, the lubricating oil composition with the prior art cleansing and dispersing agent is insufficient in meeting the requirements set by such lubricating oil products of upgraded specification.

In addition to the adverse effects of deposit, rust on engines and gears will seriously shorten the service life of engine and gearbox, and that on some key parts will largely affect the operating performance of engine and gear box. The prior art pays a lot of attention on the cleansing performance of the lubricating oil composition, but little on the anticorrosion performance thereof.

Therefore, there is still a need for a lubricating oil composition, which not only meets today's higher and higher requirements on the cleansing and dispersing performance set by lubricating oil products of upgraded specification, and also shows excellent anticorrosion performance.

INVENTION SUMMARY

The present inventors, on the basis of the prior art, found a novel Mannich base, and further found that, by using the Mannich base as the cleansing and dispersing agent in the production of a lubricating oil composition, the aforesaid problems encountered by the prior art can be solved, and then this invention is achieved.

Specifically, this invention relates to the following aspects.

1. A lubricating oil composition, comprising a Mannich base and a lubricant base oil, wherein the Mannich base comprises the structure unit (I) and the structure unit (II),

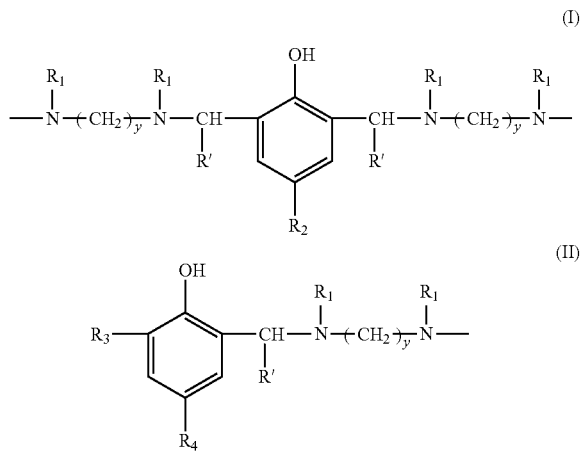

wherein, multiple $R_1$ may be the same as or different from one another, each independently selected from the group consisting of hydrogen, a $C_{1-4}$ linear or branched alkyl and a single bond, preferably each independently selected from the group consisting of hydrogen, methyl and a single bond, more preferably each independently selected from the group consisting of hydrogen and a single bond; multiple R' may be the same as or different from one another, each independently selected from the group consisting of hydrogen and a $C_{1-6}$ linear or branched alkyl, preferably each independently selected from the group consisting of hydrogen and methyl, more preferably hydrogen; $R_2$ represents a $C_{1-12}$ linear or branched alkyl, more preferably a $C_{5-12}$ linear or branched alkyl; $R_3$ represents a $C_{1-6}$ linear or branched alkyl, preferably a $C_{1-4}$ linear or branched alkyl, more preferably methyl; $R_4$ represents a hydrocarbyl having a number-averaged molecular weight Mn of 300-3000 (preferably 500-2000, more preferably 500-1500); multiple y may be the same as or different from one another, each independently selected from an integer of from 2 to 5, preferably 2 or 3.

2. The lubricating oil composition according to any one of the proceeding aspects, wherein the Mannich base is represented by the following formula (III):

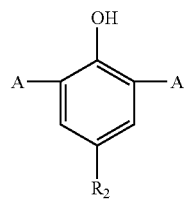

(III)

wherein, multiple A may be the same as or different from one another, each independently selected from the group consisting of

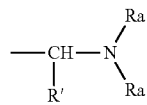

and hydrogen, preferably

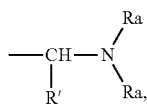

with the proviso that at least one A

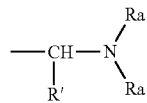

represents; multiple R' may be the same as or different from one another, each independently selected from the group consisting of hydrogen and a $C_{1-6}$ linear or branched alkyl, preferably each independently selected from the group consisting of hydrogen and methyl, more preferably hydrogen; multiple $R_a$ may be the same as or different from one another, each independently selected from the group consisting of hydrogen, a $C_{1-4}$ linear or branched alkyl and

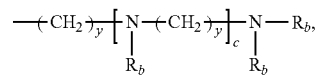

preferably each independently selected from the group consisting of hydrogen, methyl and

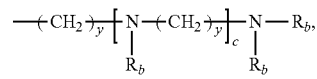

more preferably each independently selected from the group consisting of hydrogen and

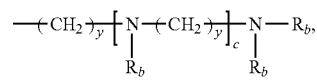

with the proviso that at least one $R_a$ represents

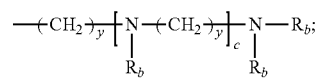

multiple $R_b$ may be the same as or different from one another, each independently selected from the group consisting of hydrogen,

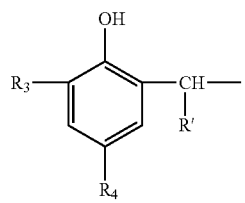

and a $C_{1-4}$ linear or branched alkyl, preferably each independently selected from the group consisting of hydrogen,

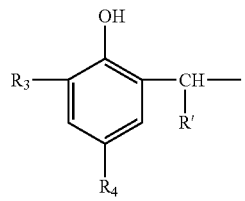

and methyl, more preferably each independently selected from the group consisting of hydrogen and

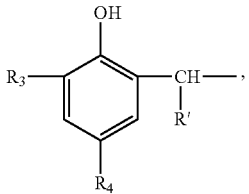

with the proviso that at least one $R_b$ represents

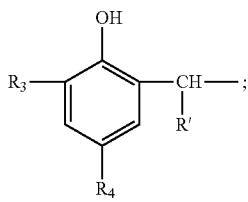

$R_2$ represents a $C_{1-12}$ linear or branched alkyl, more preferably a $C_{5-12}$ linear or branched alkyl; $R_3$ represents a $C_{1-6}$ linear or branched alkyl, preferably a $C_{1-4}$ linear or branched alkyl, more preferably methyl; $R_4$ represents a hydrocarbyl having a number-averaged molecular weight Mn of 300-3000 (preferably 500-2000, more preferably 500-1500); multiple y may be the same as or different from one another, each independently selected from an integer of from 2 to 5, preferably 2 or 3; multiple c may be the same as or different from one another, each independently selected from an integer of from 0 to 10, preferably each independently selected from an integer of from 2 to 5, more preferably 2 or 3.

3. The lubricating oil composition according to any one of the proceeding aspects, wherein the Mannich base is produced by a process comprising the step of reacting a phenolic compound of the formula (V), a phenolic compound of the formula (VI), a polyalkylenepolyamine of the formula (VII) and a $C_1$-$C_7$ linear or branched saturated aliphatic aldehyde (preferably acetaldehyde or formaldehyde, more preferably formaldehyde, especially in the form of aqueous formaldehyde solution, polyformaldehyde or paraformaldehyde) to conduct a Mannich reaction,

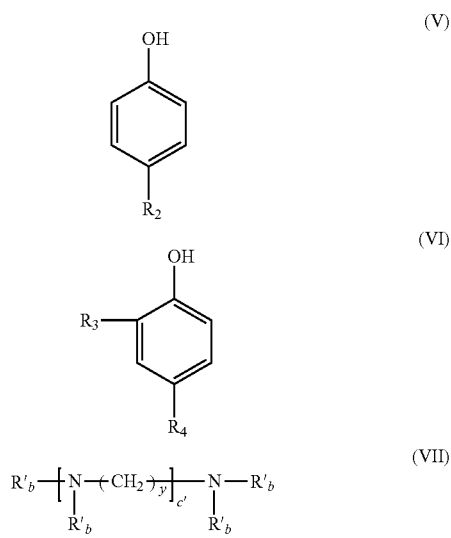

wherein, $R_2$ represents a $C_{1-12}$ linear or branched alkyl, more preferably a $C_{5-12}$ linear or branched alkyl; $R_3$ represents a $C_{1-6}$ linear or branched alkyl, preferably a $C_{1-4}$ linear or branched alkyl, more preferably methyl; $R_4$ represents a hydrocarbyl having a number-averaged molecular weight Mn of 300-3000 (preferably 500-2000, more preferably 500-1500); multiple $R_b'$ may be the same as or different from one another, each independently selected from the group consisting of hydrogen and a $C_{1-4}$ linear or branched alkyl, preferably each independently selected from the group consisting of hydrogen and methyl, more preferably hydrogen, with the proviso that at least two of $R_b'$ are hydrogen, more preferably at least one of the multiple $R_b'$ at each terminal of the molecular chain of the polyalkylenepolyamine of the formula (VII) represents hydrogen; y represents an integer of from 2 to 5, preferably 2 or 3; c' represents an integer of from 1 to 11, preferably an integer of from 3 to 6, more preferably 3 or 4.

4. The lubricating oil composition according to any one of the proceeding aspects, wherein the process is conducted in line with any one of the following ways:

Way (1) comprising the following steps:
the first step: reacting the phenolic compound of the formula (VI), the polyalkylenepolyamine of the formula (VII) and the $C_1$-$C_7$ linear or branched saturated aliphatic aldehyde at a reaction temperature of 50 to 200 degrees Celsius (preferably 60 to 150 degrees Celsius, most preferably 80 to 130 degrees Celsius) to conduct a Mannich reaction, to produce an intermediate; and the second step: reacting the intermediate, the phenolic compound of the formula (V) and the $C_1$-$C_7$ linear or branched saturated aliphatic aldehyde at a reaction temperature of 40 to 200 degrees Celsius (preferably 60 to 150 degrees Celsius, most preferably 80 to 130 degrees Celsius) to conduct a Mannich reaction, so as to produce the Mannich base, or Way (2) comprising the following steps:
the first step: reacting the phenolic compound of the formula (V), the polyalkylenepolyamine of the formula (VII) and the $C_1$-$C_7$ linear or branched saturated aliphatic aldehyde at a reaction temperature of 40 to 200 degrees Celsius (preferably 60 to 150 degrees Celsius, most preferably 80 to 130 degrees Celsius) to conduct a Mannich reaction, to produce an intermediate; and the second step: reacting the intermediate, the phenolic compound of the formula (VI) and the $C_1$-$C_7$ linear or branched saturated aliphatic aldehyde at a reaction temperature of 50 to 200 degrees Celsius (preferably 60 to 150 degrees Celsius, most preferably 80 to 130 degrees Celsius) to conduct a Mannich reaction, so as to produce the Mannich base, or Way (3) comprising the step of reacting the phenolic compound of the formula (V), the phenolic compound of the formula (VI), the polyalkylenepolyamine of the formula (VII) and the $C_1$-$C_7$ linear or branched saturated aliphatic aldehyde at a reaction temperature of 40 to 200 degrees Celsius (preferably 60 to 150 degrees Celsius, most preferably 80 to 130 degrees Celsius) to conduct a Mannich reaction to produce the Mannich base.

5. The lubricating oil composition according to any one of the proceeding aspects, wherein in the process, in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.3-3:0.3-3.5, preferably 1:0.4-2:0.4-2.5, more preferably 1:0.5-1.5:0.5-2; in the second step of Way (1), the ratio by molar between the intermediate, the phenolic compound of the formula (V) and the $C_1$-$C_7$ linear or branched saturated aliphatic aldehyde is 1:0.2-1.5:0.2-2, preferably 1:0.3-1:0.2-1.5, more preferably 1:0.3-0.8:0.3-1.5; in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.5-2.5:1.5-3, preferably 1:1.7-2.5:1.7-2.8, more preferably 1:1.7-2.2:1.7-2.5; in the second step of Way (2), the ratio by molar between the intermediate, the phenolic compound of the formula (VI) and the $C_1$-$C_7$ linear or branched saturated aliphatic aldehyde is 1:1.5-3:1.5-3, preferably 1:1.7-2.5:1.7-3, more preferably 1:1.7-2.3:1.7-2.5; in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1-5:1-3:2-8, preferably 1:1.5-4.5:1.5-2.5:3-7, more preferably 1:1.8-4.3:1.8-2.3:3.5-6.5.

6. The lubricating oil composition according to any one of the proceeding aspects, wherein in the process, the Mannich reaction is conducted in the presence of one or more diluent selected from the group consisting of polyolefins, mineral base oils and polyethers.

7. The lubricating oil composition according to any one of the proceeding aspects, wherein in the process, the phenolic compound of the formula (VI) is produced by in the presence of an alkylating catalyst, reacting a phenolic compound of the formula (IV) with a polyolefin having a number-averaged molecular weight Mn of 300-3000 (preferably 500-2000, more preferably 500-1500) to conduct an alkylation reaction, wherein the polyolefin is preferably produced by the homopolymerization of ethylene, propylene or a $C_4$-$C_{10}$α-olefin or by the copolymerization between two or more of these olefins, more preferably polyisobutene,

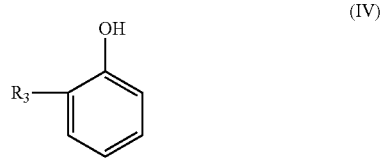

(IV)

wherein, $R_3$ is as defined in Aspect 3.

8. The lubricating oil composition according to any one of the proceeding aspects, further comprising one or more lubricating oil additives selected from the group consisting of antioxidants, dispersing agents, detergents, anti-wear agents and friction modifiers, wherein on a weight basis, the antioxidant accounts for 0-10 wt %, preferably 0.1 to 5 wt %, more preferably from 0.2 to 3 wt %, of the total weight of the lubricating oil composition, the dispersing agent accounts for 0.5 to 15 wt %, preferably 1 to 10 wt %, more preferably from 1.5 to 8 wt %, of the total weight of the lubricating oil composition, the detergent accounts for 0.2 to 20 wt %, preferably 0.8-15 wt %, and more preferably 1.2 to 10 wt %, of the total weight of the lubricating oil composition, the anti-wear agent accounts for 0.1 to 10 wt %, preferably 0.2 to 8 wt %, more preferably 0.5 to 5 wt %, of the total weight of the lubricating oil composition, the friction modifier accounts for 0.01 to 5 wt %, preferably 0.02 to 4 wt %, more preferably from 0.05 to 3 wt %, of the total weight of the lubricating oil composition.

9. The lubricating oil composition according to any one of the proceeding aspects, wherein the antioxidant is one or more selected from the group consisting of amine antioxidants, phenol-ester antioxidants, thio phenol-ester antioxidants and phenolic antioxidants, preferably one or more selected from the group consisting of amine antioxidants, phenol-ester antioxidants and phenolic antioxidants, the dispersing agent is one or more selected from the group consisting of polyisobutylene succinimide based dispersing agents, borated polyisobutylene succinimide based dispersing agents and succinic ester based dispersing agent, preferably one or more selected from the group consisting of polyisobutylene succinimide based dispersing agents and borated polyisobutylene succinimide based dispersing agent, the detergent is one or more selected from the group consisting of sulfonate detergents, alkyl phenate detergents, sulfurized alkyl phenate detergents, salicylate detergents and naphthenate detergent, preferably one or more selected from the group consisting of sulfonate detergents, sulfurized alkyl phenate detergents and salicylate detergents, the anti-wear agent is one or more selected from the group consisting of dialkyl dithiophosphate anti-wear agents, phosphoric ester type extreme pressure anti-wear agents, sulfurized olefin based anti-wear agents, dialkyl dithiocarbamate anti-wear agents and thiadiazole derivative anti-wear agents, preferably one or more selected from the group consisting of dialkyl dithiophosphate anti-wear agents, phosphoric ester type extreme pressure anti-wear agents, sulfurized olefin based anti-wear agents, and dialkyl dithiocarbamate anti-wear agents, the friction modifier is one or more selected from the group consisting of oil-soluble organo-molybdenum friction modifiers, ashless friction modifiers, and organic boronic acid ester friction modifier, preferably one or more selected from the group consisting of oil-soluble organo-molybdenum friction modifiers and ashless friction modifiers.

10. The lubricating oil composition according to any one of the proceeding aspects, wherein on a weight basis, the Mannich base accounts for 0.01-20 wt %, preferably 0.02-16 wt %, more preferably 0.1-15 wt %, of the total weight of the lubricating oil composition 11. A process for producing the lubricating oil composition according to any one of the proceeding aspects, comprising the step of mixing the Mannich base and the lubricant base oil.

Technical Effects

The lubricating oil composition of this invention exhibits excellent cleansing and dispersing performance and excellent anticorrosion performance, whereby sufficiently meeting the requirements set by gasoline engine oils of the SL/GF-3, SM/GF-4, SN/GF-5 or greater specification, diesel engine oils of the CH-4, CI-4, CJ-4 or greater specification, methanol fuel engine oils, gas engine oils, marine cylinder oils, two-stroke engine oils, four-stroke motorcycle oils or gear oils.

FIGURE DESCRIPTION

Figure 3:
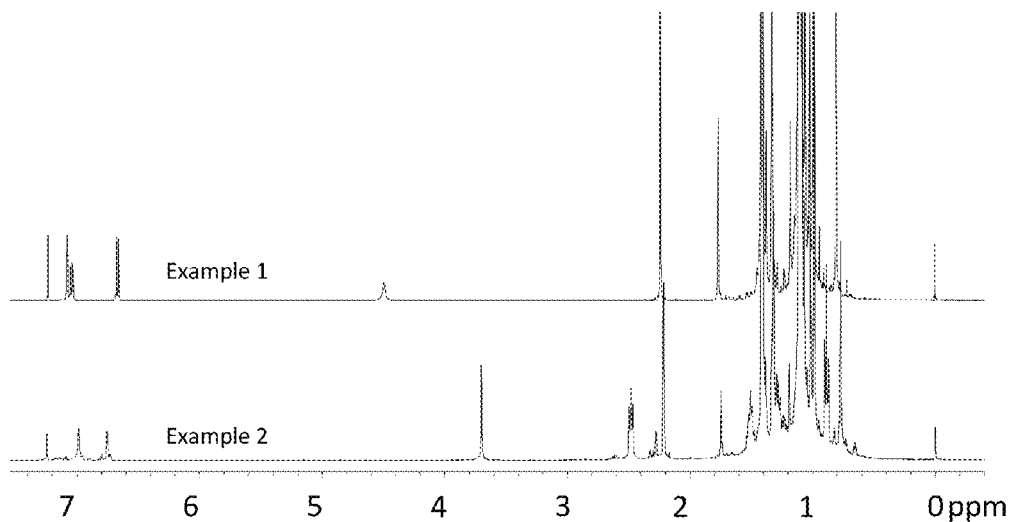

FIG. 3 compares the 1H NMR spectrum of the Mannich base produced in Example 2 with that of the polyisobutenyl o-cresol produced in Example 1.

Figure 4:
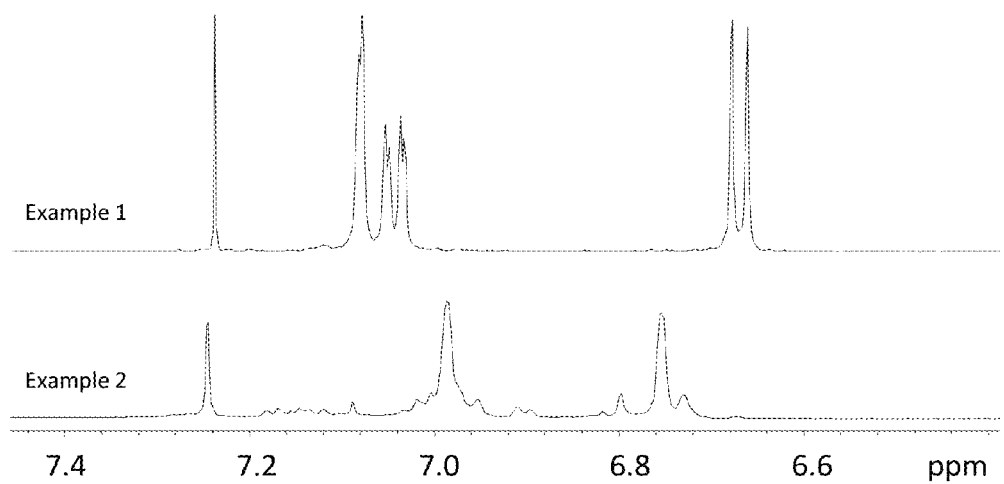

FIG. 4 compares the benzene ring region in the 1H NMR spectrum of the Mannich base produced in Example 2 and that of the polyisobutenyl o-cresol produced in Example 1.

Figure 5:
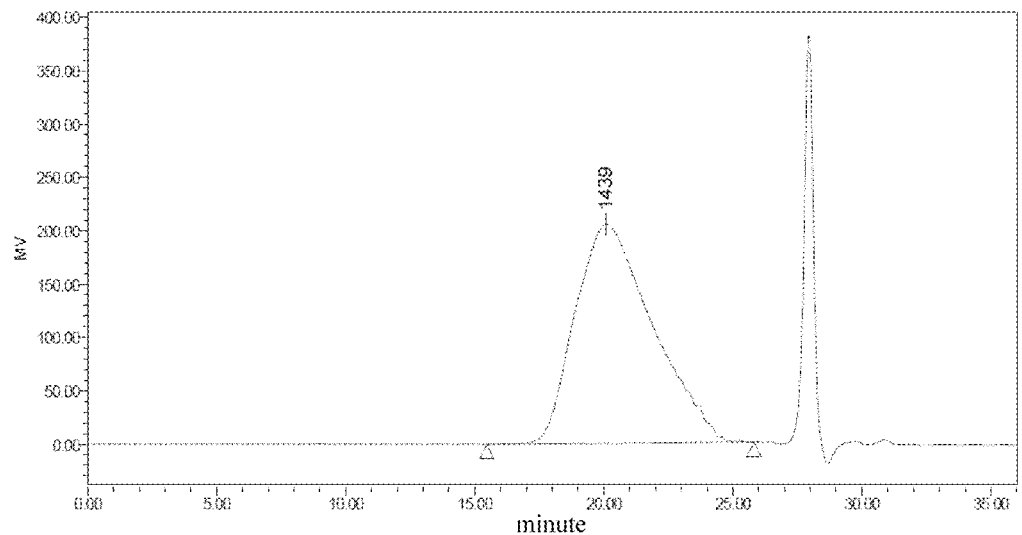

FIG. 5 illustrates the GPC spectrum of the polyisobutenyl o-cresol produced in Example 1.

Figure 6:
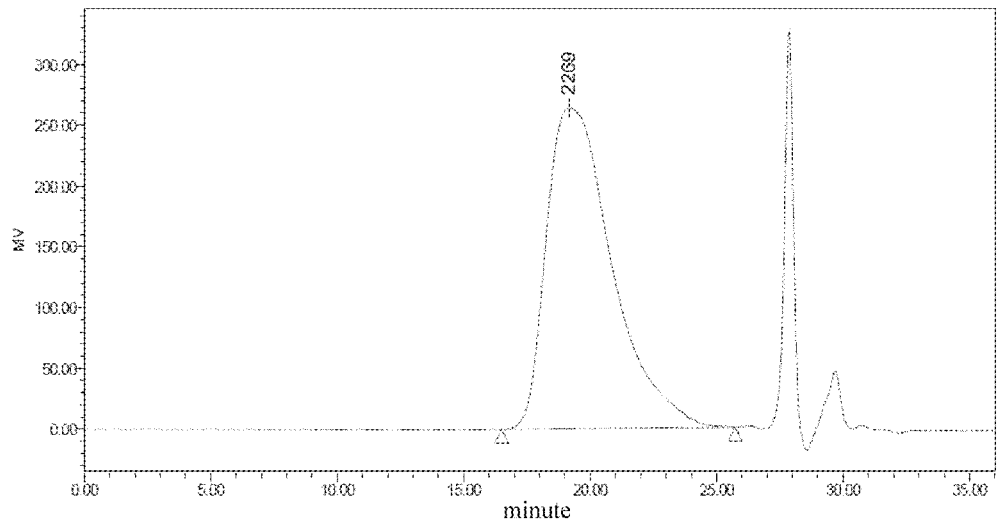

FIG. 6 illustrates the GPC spectrum of the Mannich base produced in Example 2.

Figure 7:
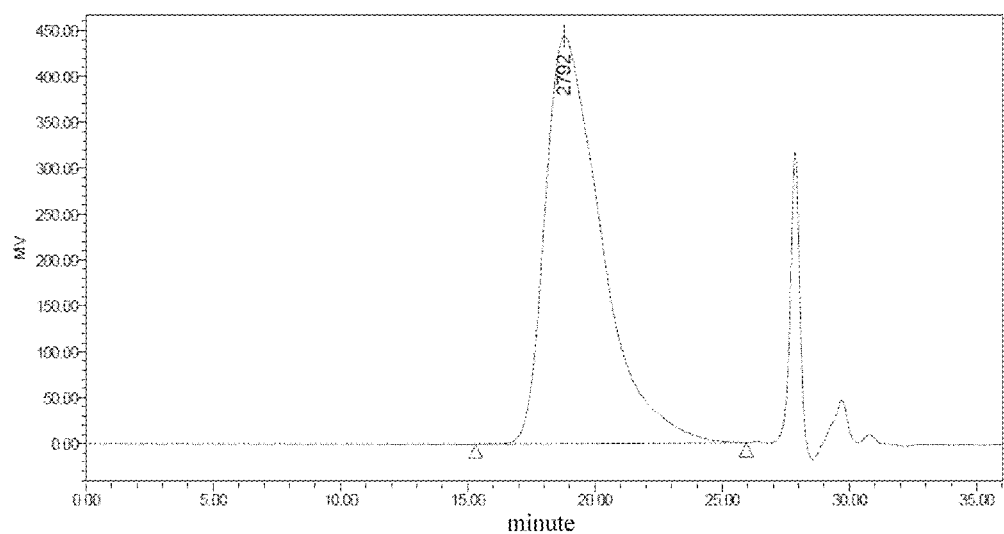

FIG. 7 illustrates the GPC spectrum of the Mannich base produced in Example 5.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims. Every document cited herein, comprising any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

In the context of this invention, when an expression like "conventionally known in this field" or "conventionally used in this field" or the like is used to describe/define an item like a material, a process, a part, an apparatus or a device, it means that this item (1) has been well known for a similar purpose in this field before this application, or (2) has not been that much well known for a similar purpose in this field before this application but gets well known for a similar purpose in this field after this application.

Unless otherwise specified, percents, parts or ratios or the like mentioned in this specification are all on a weight basis.

In the context of this specification, unless otherwise specified, the number-average molecular weight (Mn) is determined by gel permeation chromatography (GPC).

In the context of this specification, unless otherwise specified, the gel permeation chromatography is performed on Waters 2695 Gel Permeation Chromatograph (from Waters, USA), with a mobile phase of tetrafuran, a flow rate of 1 mL/min, a column temperature of 35 degrees Celsius, an elution time of 40 min, and a weight fraction of the sample of from 0.16% to 0.20%.

According to this invention, related to is a Mannich base comprising the structure unit (I) and the structure unit (II):

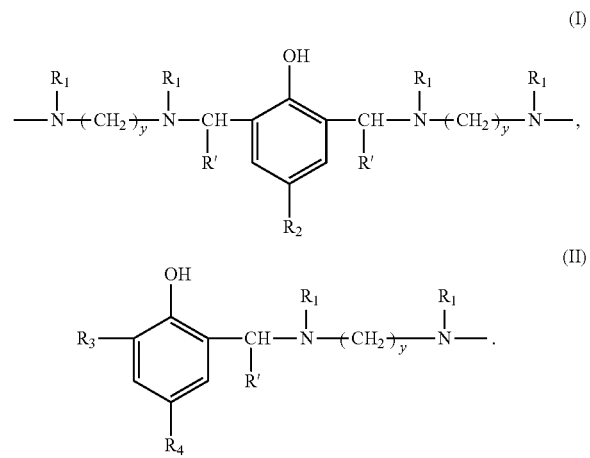

In these structure units, multiple $R_1$ may be the same as or different from one another, each independently selected from the group consisting of hydrogen, a $C_{1-4}$ linear or branched alkyl and a single bond; multiple R' may be the same as or different from one another, each independently selected from the group consisting of hydrogen and a $C_{1-6}$ linear or branched alkyl; $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5.

According to this invention, multiple $R_1$ is preferably each independently selected from the group consisting of hydrogen, methyl and a single bond, more preferably each independently selected from the group consisting of hydrogen and a single bond.

According to an embodiment of this invention, as for the p-alkyl phenol unit at the center of the structure unit (I), it is preferred that one of the two $R_1$ on the left side thereof represents a single bond, while the other of the two represents methyl or hydrogen, and one of the two $R_1$ on the right side thereof represents a single bond, while the other of the two represents methyl or hydrogen.

Further, in the structure unit (II), it is preferred that one of the two $R_1$ represents a single bond, while the other of the two represents methyl or hydrogen.

According to this invention, multiple R' may be the same as or different from one another, preferably the same as one another, and preferably each independently selected from the group consisting of hydrogen and methyl, more preferably hydrogen.

According to this invention, $R_2$ preferably represents a $C_{5-12}$ linear or branched alkyl, more preferably a $C_{8-12}$ linear or branched alkyl, for example, octyl, decyl, nonyl, undecyl or dodecyl, especially a linear octyl, decyl, nonyl, undecyl or dodecyl.

According to this invention, $R_3$ preferably represents a $C_{1-4}$ linear or branched alkyl, more preferably methyl or ethyl.

According to this invention, as the hydrocarbyl having a number-averaged molecular weight Mn of 300-3000, there is exemplified a hydrocarbyl obtained by removing from a polyolefin having a number-averaged molecular weight Mn of 300-3000 (especially from a terminal of the polyolefin molecular chain) one hydrogen atom, hereinafter referred to as polyolefin residue group. Herein, the number-averaged molecular weight Mn of the polyolefin or the polyolefin residue group is preferably 500-2000, more preferably 500-1500. As the polyolefin, there is exemplified a polyolefin produced by the homopolymerization of ethylene, propylene or a $C_4$-$C_{10}$ α-olefin (for example, n-butene, iso-butene, n-pentene, n-hexene, n-octene or n-decene) or by the copolymerization between two or more of these olefins, more preferably a polyisobutene (PIB).

According to this invention, multiple y may be the same as or different from one another, preferably the same as one another, preferably 2 or 3, more preferably 2.

According to this invention, by "Mannich base comprising the structure unit (I) and the structure unit (II)" or the like, it means that the structure unit (I) and the structure unit (II) can be identified/detected to co-exist in the Mannich base. To this end, according to this invention, the Mannich base could be a compound of one kind, from the molecular structure of which, both of these two structure units could be detected or identified, which means that, these two structure units co-exist in the molecular structure of this compound.

Or alternatively, according to this invention, the Mannich base may be a mixture of compounds of different kinds, with the only proviso that these two structure units could be detected or identified from this mixture. Under this circumstance, these two structure units may co-exist in the molecular structure of one single compound (as preferred by this invention), or be separately comprised in the molecular structure of different compounds. Or preferably, the Mannich base according to this invention may be a mixture of compounds of different kinds, wherein the mixture comprises at least one compound, in the molecular structure of which these two structure units co-exist. The detection or identification method to be used herein has been well known in this field, including but not limiting to $^1$H-NMR or gel permeation chromatography (GPC).

According to this invention, when co-existing in the molecular structure of a single compound, these two structure units could directly bond to each other by sharing the moiety

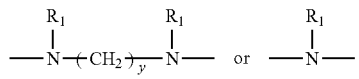

commonly comprised in both structure units, or indirectly bond to each other at the position represented by the single bond or $R_1$ (only when $R_1$ represents a single bond) on each structure unit through a connecting unit

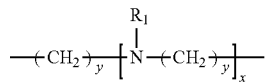

(Herein, y is as hereinbefore defined, and preferably the same as that in the structure unit (I) or the structure unit (II); $R_1$ is as hereinbefore defined; x is an integer of from 0 to 8, preferably an integer of from 0 to 3, more preferably 1).

According to this invention, in the Mannich base, the ratio by molar of the structure unit (I) and the structure unit (II) may be generally 1:1 to 1:15, preferably 1:1 to 1:8, more preferably 1:2 to 1:6, or 1:2 to 1:4.

According to an embodiment of this invention, the Mannich base is substantially consisted of the structure unit (I), the structure unit (II) and optionally the connecting unit. By "substantially" herein, it means that, any other structure unit or moiety than the structure unit (I), the structure unit (II) and the connecting unit, if does exist, only accounts for 5 mol % or less, preferably 2 mol % or less, more preferably 0.5 mol % or less, of the Mannich base as a whole, or only exists as unavoidable impurities.

According to an embodiment of this invention, the Mannich base is represented by the following formula (III).

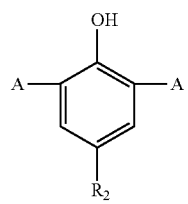

(III)

In the formula, multiple A may be the same as or different from one another, each independently selected from the group consisting of

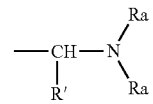

and hydrogen, with the proviso that at least one A represents

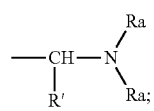

multiple R' may be the same as or different from one another, each independently selected from the group consisting of hydrogen and a $C_{1-6}$ linear or branched alkyl; multiple $R_a$ may be the same as or different from one another, each independently selected from the group consisting of hydrogen, a $C_{1-4}$ linear or branched alkyl and

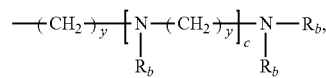

with the proviso that at least one $R_a$ represents

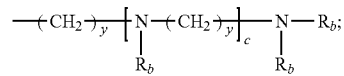

multiple $R_b$ may be the same as or different from one another, each independently selected from the group consisting of hydrogen,

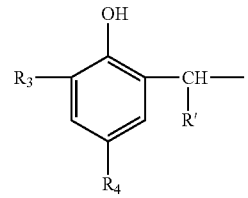

and a $C_{1-4}$ linear or branched alkyl, with the proviso that at least one $R_b$ represents

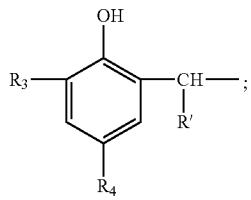

$R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-

3000; multiple y may be the same as or different from one another, each independently selected from an integer of from 2 to 5; multiple c may be the same as or different from one another, each independently selected from an integer of from 0 to 10.

According to this invention, multiple A is preferably the same as one another, more preferably all being

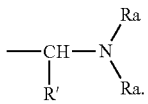

According to this invention, multiple R' may be the same as or different from one another (preferably the same as one another), and preferably each independently selected from the group consisting of hydrogen and methyl, more preferably hydrogen.

According to this invention, multiple $R_a$ is preferably each independently selected from the group consisting of hydrogen, methyl and

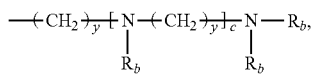

more preferably each independently selected from the group consisting of hydrogen and

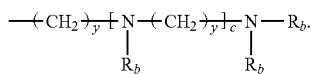

In each of the moiety

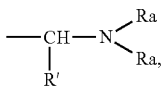

preferably one of the $R_a$ represents

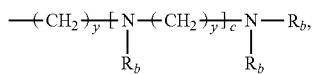

while the other of the $R_a$ represents hydrogen or methyl, or both $R_a$ represent

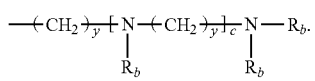

According to this invention, multiple $R_b$ is preferably each independently selected from the group consisting of hydrogen,

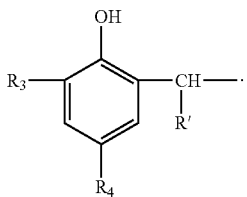

and methyl, more preferably each independently selected from the group consisting of hydrogen and

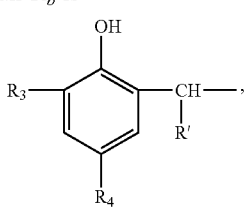

According to this invention, in the formula (III), preferably 1 to 15 out of all $R_b$ is

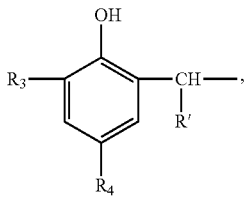

or 1 to 8 out of all $R_b$ is

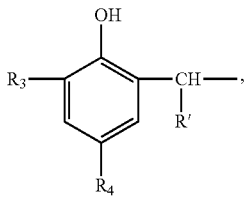

or 2 to 6 out of all $R_b$ is

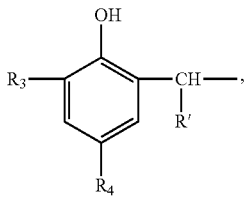

or 2 to 4 out of all $R_b$ is

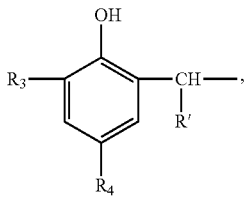

or 4 out of all $R_b$ is

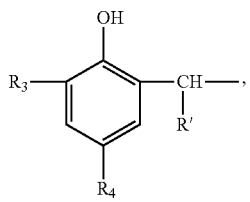

while the remaining $R_b$ represent hydrogen or methyl.

According to this invention, $R_2$ preferably represents a $C_{5-12}$ linear or branched alkyl, more preferably a $C_{8-12}$ linear or branched alkyl, for example, octyl, decyl, nonyl, undecyl or dodecyl, especially a linear octyl, decyl, nonyl, undecyl or dodecyl.

According to this invention, $R_3$ preferably represents a $C_{1-4}$ linear or branched alkyl, more preferably methyl or ethyl.

According to this invention, as the hydrocarbyl having a number-averaged molecular weight Mn of 300-3000, there is exemplified a hydrocarbyl obtained by removing from a polyolefin having a number-averaged molecular weight Mn of 300-3000 (especially from a terminal of the polyolefin molecular chain) one hydrogen atom, hereinafter referred to as polyolefin residue group. Herein, the number-averaged molecular weight Mn of the polyolefin or the polyolefin residue group is preferably 500-2000, more preferably 500-1500. As the polyolefin, there is exemplified a polyolefin produced by the homopolymerization of ethylene, propylene or a $C_4$-$C_{10}$ α-olefin (for example, n-butene, iso-butene, n-pentene, n-hexene, n-octene or n-decene) or by the copolymerization between two or more of these olefins, more preferably a polyisobutene (PIB).

According to this invention, multiple y may be the same as or different from one another, preferably the same as one another, preferably 2 or 3, more preferably 2.

According to this invention, multiple c may be the same as or different from one another, preferably each independently selected from an integer of from 2 to 5, more preferably 2 or 3.

According to this invention, the aforesaid Mannich base could be present, produced or used as individual (pure) compounds or as a mixture (at any ratio therebetween) thereof, both of which are acceptable to this invention.

According to this invention, the aforesaid Mannich base could be produced by e.g. the following process.

According to this invention, the process comprises the step of reacting a phenolic compound of the formula (V), a phenolic compound of the formula (VI), a polyalkylenepolyamine of the formula (VII) and a $C_1$-$C_7$ linear or branched saturated aliphatic aldehyde to conduct a Mannich reaction.

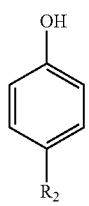

(V)

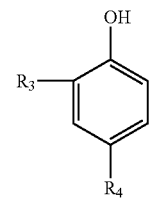

(VI)

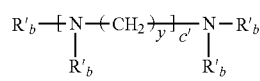

(VII)

In these formulae, $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple $R_b'$ may be the same as or different from one another, each independently selected from the group consisting of hydrogen and a $C_{1-4}$ linear or branched alkyl, with the proviso that at least two of $R_b'$ represent hydrogen; y represents an integer of from 2 to 5; c' represents an integer of from 1 to 11.

According to this invention, $R_2$ preferably represents a $C_{5-12}$ linear or branched alkyl, more preferably a $C_{8-12}$ linear or branched alkyl, for example, octyl, decyl, nonyl, undecyl or dodecyl, especially a linear octyl, decyl, nonyl, undecyl or dodecyl.

According to this invention, $R_3$ preferably represents a $C_{1-4}$ linear or branched alkyl, more preferably methyl or ethyl.

According to this invention, as the hydrocarbyl having a number-averaged molecular weight Mn of 300-3000, there is exemplified a hydrocarbyl obtained by removing from a polyolefin having a number-averaged molecular weight Mn of 300-3000 (especially from a terminal of the polyolefin molecular chain) one hydrogen atom, hereinafter referred to as polyolefin residue group. Herein, the number-averaged molecular weight Mn of the polyolefin or the polyolefin residue group is preferably 500-2000, more preferably 500-1500.

In the context of this invention, depending on the nature of the starting polyolefin or the process for producing the starting polyolefin, the polyolefin residue group may represent a saturated chain (presenting as a long alkyl chain), or may contain certain amounts of ethylenic double bond along the polymer chain (for example, those remained or produced from the production thereof), which is acceptable to this invention and will not (significantly) compromise the performance of this invention. For this reason, it is unnecessary to specify herein at what amount this ethylenic double bond may be.

As the polyolefin, there is exemplified a polymer produced by the homopolymerization of ethylene, propylene or a $C_4$-$C_{10}$ α-olefin (for example, n-butene, iso-butene, n-pentene, n-hexene, n-octene or n-decene) or that produced by the copolymerization between two or more of these olefins, more preferably a polyisobutene (PIB).

According to this invention, the phenolic compound of the formula (VI) could be produced by in the presence of an alkylating catalyst, reacting a phenolic compound of the formula (IV) with the polyolefin having a number-averaged molecular weight Mn of 300-3000 (preferably 500-2000, more preferably 500-1500) to conduct an alkylation reaction. Of course, the phenolic compound of the formula (VI) could be commercially available.

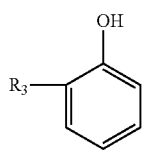

(IV)

In this formula, $R_3$ is as defined in the formula (VI), more preferably methyl.

According to this invention, the polyolefin is preferably one produced by the homopolymerization of ethylene, propylene or a $C_4$-$C_{10}$ α-olefin or that produced by the copolymerization between two or more of these olefins. As the $C_4$-$C_{10}$ α-olefin, there is exemplified n-butene, iso-butene, n-pentene, n-hexene, n-octene and n-decene.

According to this invention, at least 20 wt % (preferably at least 50 wt %, more preferably at least 70 wt %) of the polymer chain from these polyolefins comprises an ethylenic double bond at the terminal thereof. The ethylenic double bond generally presents in the form of high reactive vinylene or vinyl.

According to this invention, the polyolefin is more preferably polybutene. Unless otherwise specified, the term "polybutene" used herein covers any polymer produced by the homopolymerization of 1-butene or iso-butene, and any polymer produced by the copolymerization between two or more of 1-butene, 2-butene and iso-butene. The commercially available product thereof may contain other olefin unit(s) with a minor amount, which is acceptable by this invention.

According to this invention, the polyolefin is more preferably polyisobutene (PIB) or high reactive polyisobutene (HR-PIB). In this polyisobutene, at least 20 wt % (preferably at least 50 wt %, more preferably at least 70 wt %) of the total terminal ethylenic double bond is provided by methyl vinylene.

As the alkylating catalyst, there is exemplified one or more selected from Lewis acid catalysts, or specifically, from aluminium trichloride, boron trifluoride, tin tetrachloride, titanium tetrabromide, boron trifluoride•phenol, boron trifluoride•alcohol complex and boron trifluoride•ether complex, preferably boron trifluoride•diethyl ether complex and/or boron trifluoride•methanol complex. As the alkylating catalyst, a commercially available one could be used as such.

According to this invention, in the alkylation reaction, the ratio by molar between the polyolefin, the phenolic compound of the formula (IV) and the alkylating catalyst, for example, could be 1:1-3:0.1-0.5, preferably 1:1.5-3:0.1-0.4, most preferably 1:1.5-3:0.2-0.4, but not limiting thereto.

According to this invention, the reaction duration of the alkylation reaction, for example, may be generally 0.5 h-10 h, preferably 1 h-8 h, most preferably 3 h-5 h, but not limiting thereto.

According to this invention, the reaction temperature of the alkylation reaction, for example, may be generally 0 to 200 degrees Celsius, preferably 10 to 150 degrees Celsius, most preferably 20 to 100 degrees Celsius, but not limiting thereto.

According to this invention, the alkylation reaction could be conducted in the presence of a solvent. As the solvent, there is exemplified a $C_{6-10}$ alkane (for example, hexane, heptane, octane, nonane or decane), preferably hexane and heptane, more preferably hexane.

According to this invention, upon completion of the alkylation reaction, after removing the alkylating catalyst, any unreacted reactants and the optionally used solvent from the finally obtained reaction mixture by any way conventionally known in this field, the phenolic compound of the formula (VI) is obtained.

According to this invention, multiple $R_b'$ may be the same as or different from one another, preferably each independently selected from the group consisting of hydrogen and methyl. It is more preferred that the polyalkylenepolyamine of the formula (VII) has at least one of the multiple $R_b'$ at each terminal of the molecular chain thereof representing hydrogen respectively, which corresponds to the following formula (VII-1).

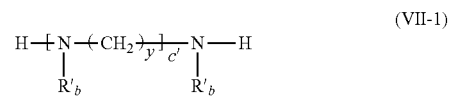

(VII-1)

In this formula, $R_b'$, y and c' are as defined in the formula (VII).

According to this invention, as the polyalkylenepolyamine, there is exemplified one or more selected from diethylenetriamine, triethylenetetramine, tetraethylenepentamine, pentaethylenehexamine, hexaethyleneheptamine, heptaethyleneoctamine, octaethylenenonamine, nonaethylenedecamine and decaethyleneundecamine, preferably diethylenetriamine.

According to this invention, the polyalkylenepolyamine could be a commercially available one or be produced by e.g. a reaction between ammonia and an alkane dihalide like an alkane dichloride.

According to this invention, y is preferably 2 or 3.

According to this invention, c' is preferably an integer of from 3 to 6, more preferably 3 or 4.

According to this invention, the $C_1$-$C_7$ linear or branched saturated aliphatic aldehyde is preferably acetaldehyde or formaldehyde, more preferably formaldehyde. As the formaldehyde, an aqueous solution of formaldehyde, polyformaldehyde or paraformaldehyde could be exemplified, without any specific limitation.

According to this invention, the process could be conducted in line with any one of the following ways.

Way (1) comprising the following steps:
the first step: reacting the phenolic compound of the formula (VI), the polyalkylenepolyamine of the formula (VII) and the $C_1$-$C_7$ linear or branched saturated aliphatic aldehyde at a reaction temperature of 50 to 200 degrees Celsius (preferably 60 to 150 degrees Celsius, most preferably 80 to 130 degrees Celsius) to conduct a Mannich reaction, to produce an intermediate; and
the second step: reacting the intermediate, the phenolic compound of the formula (V) and the $C_1$-$C_7$ linear or branched saturated aliphatic aldehyde at a reaction temperature of 40 to 200 degrees Celsius (preferably 60 to 150 degrees Celsius, most preferably 80 to 130 degrees Celsius) to conduct a Mannich reaction, so as to produce the Mannich base.

Way (2) comprising the following steps:
the first step: reacting the phenolic compound of the formula (V), the polyalkylenepolyamine of the formula (VII) and the $C_1$-$C_7$ linear or branched saturated aliphatic aldehyde at a reaction temperature of 40 to 200 degrees Celsius (preferably 60 to 150 degrees Celsius, most preferably 80 to 130 degrees Celsius) to conduct a Mannich reaction, to produce an intermediate; and the second step: reacting the intermediate, the phenolic compound of the formula (VI) and the $C_1$-$C_7$ linear or branched saturated aliphatic aldehyde at a reaction temperature of 50 to 200 degrees Celsius (preferably 60 to 150 degrees Celsius, most preferably 80 to 130 degrees Celsius) to conduct a Mannich reaction, so as to produce the Mannich base.

Way (3) comprising a step of reacting the phenolic compound of the formula (V), the phenolic compound of the formula (VI), the polyalkylenepolyamine of the formula (VII) and the $C_1$-$C_7$ linear or branched saturated aliphatic aldehyde at a reaction temperature of 40 to 200 degrees Celsius (preferably 60 to 150 degrees Celsius, most preferably 80 to 130 degrees Celsius) to conduct a Mannich reaction, so as to produce the Mannich base.

According to this invention, from the standpoint of obtaining a Mannich base with a relatively higher purity, Way (1) is preferred.

According to this invention, in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.3-3:0.3-3.5, preferably 1:0.4-2:0.4-2.5, more preferably 1:0.5-1.5:0.5-2. There is no specific limitation as to the time duration of this step, which may be generally 1 h-10 h, preferably 2 h-8 h, most preferably 3 h-6 h.

According to this invention, in the second step of Way (1), the ratio by molar between the intermediate, the phenolic compound of the formula (V) and the $C_1$-$C_7$ linear or branched saturated aliphatic aldehyde is 1:0.2-1.5:0.2-2, preferably 1:0.3-1:0.2-1.5, more preferably 1:0.3-0.8:0.3-1.5. There is no specific limitation as to the time duration of this step, which may be generally 1 h-10 h, preferably 2 h-8 h, most preferably 3 h-6 h.

According to this invention, in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.5-2.5:1.5-3, preferably 1:1.7-2.5:1.7-2.8, more preferably 1:1.7-2.2:1.7-2.5. There is no specific limitation as to the time duration of this step, which may be generally 1 h-10 h, preferably 2 h-8 h, most preferably 3 h-6 h.

According to this invention, in the second step of Way (2), the ratio by molar between the intermediate, the phenolic compound of the formula (VI) and the $C_1$-$C_7$ linear or branched saturated aliphatic aldehyde is 1:1.5-3:1.5-3, preferably 1:1.7-2.5:1.7-3, more preferably 1:1.7-2.3:1.7-2.5. There is no specific limitation as to the time duration of this step, which may be generally 1 h-10 h, preferably 2 h-8 h, most preferably 3 h-6 h.

According to this invention, in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1-5:1-3:2-8, preferably 1:1.5-4.5:1.5-2.5:3-7, more preferably 1:1.8-4.3:1.8-2.3:3.5-6.5. There is no specific limitation as to the time duration of Way (3), which may be generally 1 h-10 h, preferably 2 h-8 h, most preferably 3 h-6 h.

According to this invention, the aforesaid Mannich reaction could be conducted in the presence of a diluent and/or a solvent. As the diluent, there is exemplified one or more selected from polyolefins, mineral base oils and polyethers. As the solvent, there is exemplified a $C_{6-20}$ aromatic hydrocarbon (for example, toluene and xylene). Herein, toluene or xylene is preferred.

According to this invention, the diluent and/or the solvent could be added to the Mannich reaction at any stage thereof in any amount conventionally used in this field, for example, be added at the beginning of or during the first step in Way (1) and/or at the beginning of or during the second step in Way (1), at the beginning of or during the first step in Way (2) and/or at the beginning of or during the second step in Way (2), or at the beginning of or during Way (3), without any specific limitation.

According to this invention, as the mineral base oil, there is exemplified one or more selected from API Group I, API Group II or API Group III mineral lubricant base oils, preferably from mineral lubricant base oils having a viscosity of 20-120 centistokes (cSt) at 40 degrees Celsius and a viscosity index of at least 50 or more; more preferably from mineral lubricant base oils having a viscosity of 28-110 centistokes (cSt) at 40 degrees Celsius and a viscosity index of at least 80 or more.

According to this invention, as the polyolefin, there is exemplified one or more selected from a polyolefin produced by the homopolymerization of ethylene, propylene or a $C_4$-$C_{10}$ α-olefin or that produced by the copolymerization between two or more of these olefins, preferably from a poly α-olefin (PAO) having a viscosity of 2-25 centistokes (cSt) at 100 degrees Celsius (preferably that having a viscosity of 6-10 centistokes (cSt) at 100 degrees Celsius). Herein, as the $C_4$-$C_{10}$ α-olefin, there is exemplified n-butene, iso-butene, n-pentene, n-hexene, n-octene and n-decene. Further, the number-averaged molecular weight Mn of the polyolefin may be generally 500-3000, preferably 500-2500, most preferably 500-1500.

According to this invention, as the polyether, there is exemplified a polymer produced by a reaction between an alcohol and an epoxide. As the alcohol, there is exemplified ethylene glycol and/or 1,3-propylene glycol. As the epoxide, there is exemplified ethylene oxide and/or propylene oxide. Further, the number-averaged molecular weight Mn of the polyether may be generally 500-3000, preferably 700-3000, most preferably 1000-2500.

In general, the Mannich reaction is conducted under the protective atmosphere of an inert gas. As the inert gas, there is exemplified nitrogen gas or Ar gas, but without any limitation thereto.

According to this invention, upon completion of the process, after removing water and any solvent from the finally obtained reaction mixture by any way conventionally known in this field, a Mannich base is obtained.

In this context, this invention further relates to the Mannich base produced in line with the aforesaid process.

According to this invention, by the aforesaid process, as the reaction product, the Mannich base could be produced in the form of a single kind of Mannich base with relatively much higher purity (for example, 95% or more), or could be produced in the form of a mixture of two or more different Mannich bases, or could be produced in the form of a mixture of one or more Mannich base(s) with the aforesaid diluent (if any). All these forms are covered by this invention and identified as being effective and desirable in this invention. In view of this, in the context of this invention, these forms are all accepted or referred to as Mannich base of this invention without any discrimination therebetween. In this context, according to this invention, it is not absolutely necessary to further purify the reaction product, or to further isolate one or more specific Mannich base(s) from the reaction product. Of course, this purification or isolation may be preferred in some cases by this invention, however, is not absolutely necessary to this invention. Nevertheless, as the purification or isolation method, there is exemplified column chromatography or preparative chromatography.

The Mannich base of this invention is especially suitable for producing a cleansing and dispersing agent, especially a cleansing and dispersing agent for a lubricating oil, which exhibits excellent deposit formation suppressing performance and excellent anticorrosion performance.

According to this invention, the cleansing and dispersing agent comprises any of the aforesaid Mannich base (or a mixture thereof at any ratio therebetween) or any Mannich base produced in line with the aforesaid process.

According to this invention, to produce the cleansing and dispersing agent, it is acceptable to further introduce the aforesaid diluent into the Mannich base.

Herein, as the diluent, one kind or a mixture of two or more kinds at any ratio therebetween could be used. Of course, depending on the amount at which the diluent has been introduced into the Mannich base of this invention after production of same as aforesaid, the amount of diluent to be added could be reduced accordingly or even eliminated. In the latter case, the Mannich base per se could be used as a cleansing and dispersing agent without the need of adding any further diluent thereto, which is reasonable to a person skilled in the art.

In general, in the cleansing and dispersing agent of this invention, on a weight basis, the Mannich base accounts for from 10 to 70 wt %, preferably from 10 to 60 wt %, most preferably from 10 to 50 wt %, of the total weight of the cleansing and dispersing agent.

According to this invention, in order to produce the cleansing and dispersing agent, the Mannich base may be mixed with the diluent (if used) at 20-60 degrees Celsius for 1-6 h.

The Mannich base or cleansing and dispersing agent of this invention is particularly suitable for producing a lubricating oil composition, which exhibits excellent cleansing performance (i.e. the deposit formation suppressing performance) and anticorrosion performance. Accordingly, this invention further relates to a lubricating oil composition comprising any of the aforesaid Mannich base of this invention (or a mixture thereof at any ratio therebetween), a Mannich base produced in line with any of the aforesaid process, or the aforesaid cleansing and dispersing agent, and a lubricant base oil.

According to this invention, in order to produce the lubricating oil composition of this invention, any of the aforesaid Mannich base (or a mixture thereof at any ratio therebetween), the Mannich base produced in line with any of the aforesaid process of this invention, or any of the aforesaid cleansing and dispersing agent as a lubricating oil additive, may be mixed till homogenous with a lubricant base oil and optionally other lubricating oil additive (if needed) in a predetermined ratio therebetween or in predetermined amounts thereof.

More specifically, in order to produce the lubricating oil composition of this invention, the lubricating oil additives described above may be added separately to the lubricant base oil, or be made into a concentrate and then added to the lubricant base oil, and then mixed till homogenous under heat. The temperature involved herein is generally 40-90 degrees Celsius, the time duration is generally 1-6 h.

According to this invention, the Mannich base or the cleansing and dispersing agent is added such that the amount (on a weight basis) of the Mannich base or that of the cleansing and dispersing agent (calculated as the Mannich base) accounts for from 0.01 to 20 wt %, preferably from 0.02 to 16 wt %, more preferably from 0.1 to 15 wt %, of the total weight of the lubricating oil composition.

The diluents mentioned hereinbefore have been frequently used in this field as lubricant base oils, and for this reason, the diluent will not be described hereinafter as an individual component, but be integrated into the definition of lubricant base oils.

In this context, according to this invention, the lubricating oil composition of this invention comprise any of the aforesaid Mannich base (or a mixture thereof at any ratio therebetween), or the Mannich base produced in line with any of the aforesaid process of this invention, and a lubricant base oil.

According to this invention, on a weight basis, the Mannich base accounts for from 0.01 to 20 wt %, preferably from 0.02 to 16 wt %, more preferably from 0.1 to 15 wt %, of the total weight of the lubricating oil composition.

According to this invention, the lubricating oil composition may further include one or more other lubricating oil additives selected from the group consisting of antioxidants, other dispersing agents than the present Mannich base, detergents, anti-wear agents and friction modifiers.

According to this invention, the antioxidant, for example, may be one or more selected from amine antioxidants, phenol-ester antioxidants, thio phenol-ester antioxidants and phenolic antioxidants. As the amine antioxidant, there is exemplified alkylated diphenylamine antioxidants. As the alkylated diphenylamine antioxidant, there is exemplified IRGANOX L-01 (BASF), IRGANOX L-57 (BASF), T534 (Beijing Xing Pu Co. Ltd.), LZ5150A (Luborun LANLIAN Additive Co., Ltd.), VANLUBE NA (Vanderbilt (US) company), VANLUBE 961 (Vanderbilt (US) company), VANLUBE 81 (dioctyl diphenylamine), VANLUBE DND (dinonyl diphenylamine), RC7001 (German Rhein Chemie Corp., p,p'-diisooctyl diphenylamine), preferably tert-butyl/iso-octyl diphenylamine (e.g. T534 from Beijing Xing Pu Co. Ltd.). As the thio phenol-ester antioxidants, there is exemplified 2,2'-thio-bis[3-(3,5-di-tert-butyl-4-hydroxyphenyl) propionate ethyl] (e.g. Antioxidant 1035 from Sichuan Yongye Chemical Co., Ltd. or IRGANOX L115 from BASF).

According to this invention, as the antioxidant, preference is given to a combination of the alkylated diphenylamine antioxidant and the thio phenol-ester antioxidant, wherein the alkylated diphenylamine antioxidant accounts for 50-95 wt %, preferably 60-90 wt %, of the total weight of the combination, while the thio phenol-ester antioxidant accounts for 5-50 wt %, preferably 10-40 wt %, of the total weight of the combination.

According to this invention, on a weight basis, the antioxidant accounts for 0-10 wt %, preferably 0.1 to 5 wt %, more preferably from 0.2 to 3 wt %, of the total weight of the lubricating oil composition.

According to this invention, as the other dispersing agent, there is exemplified one or more selected from polyisobutylene succinimide based dispersing agents, borated polyisobutylene succinimide based dispersing agents and succinic acid ester based dispersing agent, preferably from polyisobutylene succinimide based dispersing agents and borated polyisobutylene succinimide based dispersing agent. As the polyisobutylene succinimide based dispersing agent, preference is given to polyisobutylene succinimide based ashless dispersing agents, wherein the polyisobutylene (PIB) moiety thereof has a number averaged molecular weight of 800-4000, preferably 900-3000, more preferably 1000-2400, for example, T161 (Suzhou special oil factory), T161A (Jinzhou Petrochemical Company additive factory), T161B (Jinzhou Petrochemical Company additive factory), LZLI57 (Luborun LANLIAN Additive Co., Ltd.), LZ6418 (Lubrizol Corp.), LZ6420 (Lubrizol Corp.), Hitec646 (Afton chemical company). As the borated polyisobutenyl succinimide based dispersing agent, preference is given to one wherein the polyisobutylene moiety thereof has a number averaged molecular weight of 500-4000, preferably 700-2500, preferably 1000-2300, for example, MX3316 (Agip Petroli company), Hitec648 (Afton chemical company), Hitec7714 (Afton chemical company) and LZ935 (Lubrizol Corp.).

According to this invention, preference is given to a combination of the polyisobutylene succinimide based ashless dispersing agent and the borated polyisobutylene succinimide based dispersing agent, wherein the ratio by weight therebetween in the combination may be generally 1:1 to 3:1.

According to this invention, on a weight basis, the dispersing agent accounts for 0.5 to 15 wt %, preferably 1 to 10 wt %, more preferably from 1.5 to 8 wt %, of the total weight of the lubricating oil composition.

According to this invention, as the detergent, there is exemplified one or more selected from sulfonate detergents, alkyl phenate detergents, sulfurized alkyl phenate detergents, salicylate detergents and naphthenate detergents, preferably from sulfonate detergents, sulfurized alkyl phenate detergents and salicylate detergents. As the sulfonate detergent, there is exemplified calcium sulfonate. As the sulfurized alkyl phenate detergents, there is exemplified calcium sulfurized alkyl phenate. Preference is given to a mixture of calcium sulfonate having an alkali value of 100-450 mgKOH/g and calcium sulfurized alkyl phenate, preferably a mixture of a high alkali value calcium sulfonate having an alkali value of 200-450 mgKOH/g and a medium alkali value calcium sulfurized alkyl phenate having an alkali value of from 100 to less than 200 mgKOH/g, with a ratio by weight therebetween of 0.2:1 to 4:1, preferably 0.5:1 to 2:1. As calcium sulfonate and calcium sulfurized alkyl phenate, there is exemplified T101 (Shanghai coking additive factory), T102 (Shanghai coking additive factory), T103 (Shanghai coking additive factory), T106 (Jinzhou Petrochemical Company additive factory), LZ6478 (Lubrizol Corporation), LZ6446 (Lubrizol Corporation), LZ75 (Lubrizol Corporation), LZ78 (Lubrizol Corporation), Hitec611 (Afton Corporation), Hitec614 (Afton Corporation), LZL115A (Luborun LANLIAN Additive Co., Ltd.), LZL115B (Luborun LANLIAN Additive Co., Ltd.), LZ6477 (Lubrizol Corporation), LZ6578 (Lubrizol Corporation), and OLOA219 (Chevron Co.).

According to this invention, on a weight basis, the detergent accounts for 0.2 to 20 wt %, preferably 0.8-15 wt %, and more preferably 1.2 to 10 wt %, of the total weight of the lubricating oil composition.

According to this invention, as the anti-wear agent, there is exemplified one or more selected from dialkyl dithiophosphate anti-wear agents, phosphoric ester type extreme pressure anti-wear agents, sulfurized olefin based anti-wear agents, dialkyl dithiocarbamate anti-wear agents and thiadiazole derivative anti-wear agents, preferably from dialkyl dithiophosphate anti-wear agents, phosphoric ester type extreme pressure anti-wear agents, sulfurized olefin based anti-wear agents, and dialkyl dithiocarbamate anti-wear agents. As the dialkyl dithiophosphate anti-wear agent, there is exemplified zinc dialkyl dithiophosphate having an alkyl containing 2-12 carbon atoms, preferably containing 2-8 carbon atoms, such as ethyl, n-propyl, isopropyl, n-butyl, isobutyl, sec-butyl, n-pentyl, isopentyl, n-hexyl, isohexyl, n-octyl, 2-ethylhexyl, cyclohexyl, methyl cyclopentyl. As the zinc dialkyl dithiophosphate, there is exemplified T202 (Wuxi Nanfang Petroleum Additive Co., Ltd.), T203 (Wuxi Nanfang Petroleum Additive Co., Ltd.), T202 (Jinzhou Petrochemical Company additive factory), T203 (Jinzhou Petrochemical Company additive factory), T204 (Jinzhou Petrochemical Company additive factory), T205 (Jinzhou Petrochemical Company additive factory), LZ1371 (Lubrizol Corp.), LZ1375 (Lubrizol Corp.), C9417 (Infineum company), C9425 (Infineum company), C9426 (Infineum company), Hitec 7169 (Afton Corporation), and Hitec1656 (Afton Corporation). As the phosphoric ester type extreme pressure anti-wear agent, there is exemplified one or more selected from triphenyl phosphite, tritolyl phosphite, trisdodecyl phosphite, tris-octadecyl phosphite, for example, Irgafos DDPP (BASF), Irgafos OPH (BASF), or Irgafos TNPP (BASF).

According to this invention, on a weight basis, the anti-wear agent accounts for 0.1 to 10 wt %, preferably 0.2 to 8 wt %, more preferably 0.5 to 5 wt %, of the total weight of the lubricating oil composition.

According to this invention, as the friction modifier, there is exemplified one or more selected from oil-soluble organo-molybdenum friction modifiers, ashless friction modifiers, and organic boronic acid ester friction modifier, preferably from oil-soluble organo-molybdenum friction modifiers and ashless friction modifiers. As the oil-soluble organo-molybdenum friction modifier, there is exemplified one or more selected from molybdenum dialkyl dithiophosphate, molybdenyl dialkyl dithiophosphate, molybdenum dialkyl dithiocarbamate, molybdenum xanthate, molybdenum thioxanthate, trinuclear molybdenum sulfide complexes, molybdenum-amine complexes and molybdate ester based oil-soluble organo-molybdenum friction modifiers. The organo-molybdenum friction modifier has an organic group having sufficient numbers of carbon atom such that the organo-molybdenum friction modifier can be dissolved or dispersed in a lubricant base oil, with the carbon atom number being generally 6-60, preferably 10-50. As the oil-soluble organo-molybdenum friction modifier, there is exemplified MolyVan L (Vanderbilt US company), 822 (Vanderbilt US company), 855 (Vanderbilt US company), 515 (Japan Solectron company), 525 (Japan Solectron company), 710 (Japan Solectron company). As the ashless friction modifier, there is exemplified one or more selected from polyol fatty acid esters, fatty amines and fatty amides, wherein by fatty, it refers to a saturated or unsaturated hydrocarbyl having a carbon atom number of 6-60, preferably 10-50. As the polyol fatty acid ester, there is exemplified monoesters, diesters or poly-esters like fatty acid glycerides, fatty acid pentaerythritol esters, fatty acid ethylene glycol esters, fatty acid butylene glycol esters, fatty acid ethanolamine esters, fatty acid diethanolamine esters, or fatty acid triethanolamine esters, or specifically, oleic acid monoglyceride, oleic acid diglyceride, pentaerythritol monostearate, diester of ethylene glycol and lauric acid, oleic acid monoglyceride, monoester of oleic acid and diethanolamine, monoester of triethanolamine and oleic acid. As the fatty amine, there is exemplified hydrocarbyl-substituted monoamines or polyamines, alkoxylated hydrocarbyl-substituted monoamines or polyamines, and alkyl ether amines, for example ethoxylated tallow fatty amine and ethoxylated tallow fatty ether amine. As the fatty amides, there is exemplified oleic amide, coconut amide, oleic acid diethanol amide. As the ashless friction modifier, there is exemplified F10 (BASF) and F20 (BASF).

According to this invention, preference is given to a combination of the oil-soluble organo-molybdenum friction modifier and the ashless friction modifier, wherein the oil-soluble organo-molybdenum friction modifier accounts for 5-50 wt %, preferably 10-40 wt %, of the total weight of the combination, while the ashless friction modifier accounts for 50-95 wt %, preferably 60-90 wt %, of the total weight of the combination.

According to this invention, on a weight basis, the friction modifier accounts for 0.01 to 5 wt %, preferably 0.02 to 4 wt %, more preferably from 0.05 to 3 wt %, of the total weight of the lubricating oil composition.

According to this invention, as the lubricant base oil, there is exemplified one or more selected from mineral lubricating oils and synthetic lubricating oils. As the mineral lubricating oil, there is exemplified, from the standpoint of viscosity, mineral lubricating oils ranging from light distillate mineral oils to heavy distillate mineral oils, for example liquid paraffin and hydrorefined solvent-treated paraffinic, naphthenic and mixed paraffinic-naphthenic mineral lubricating oils, usually identified as Group I, II, III base oils. Commercially available one includes Group I 150SN, 600SN, or Group II 100N, 150N. As the synthetic lubricating oil, there is exemplified polymeric hydrocarbon oils, alkyl benzenes and derivatives thereof. As the polymeric hydrocarbon oil, there is exemplified polybutylene, polypropylene, propylene-isobutylene copolymers, chlorinated polybutylene, poly(1-hexene), poly(1-octene), poly(1-decene), a commercially available one thereof including PAO4, PAO6, PAO8, or PAO10. As the alkyl benzene, there is exemplified dodecylbenzene, tetradecylbenzene, dinonylbenzene, di(2-ethylhexyl) benzene; As the alkylbenzene derivative, there is exemplified alkylated diphenyl ethers and alkylated diphenyl sulfides, and derivatives, analogs or homologs thereof. As the synthetic lubricating oil, there is further exemplified ester oils, including but not limiting to esters or complex esters resulted from a condensation reaction between dicarboxylic acids (such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid) with alcohols (e.g., butanol, hexanol, dodecanol, 2-ethylhexanol, ethylene glycol, propylene glycol), specifically dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, diester of linoleic acid dimmer and 2-ethyl hexanol. As the synthetic lubricating oil, there is further exemplified Fischer-Tropsch synthetic oils and lubricant base oils obtained by hydroisomerizating, hydrocracking or dewaxing Fischer-Tropsch synthetic oils.

According to this invention, the viscosity index of the lubricant base oil is typically greater than 80, saturated hydrocarbons are contained at a content of greater than 90 wt %, and sulfur is contained at a content of less than 0.03 wt %.

The lubricating oil composition of this invention may further contain one or more selected from metal corrosion inhibitors, rust inhibitors, pour point reducing agents and anti-foaming agents. As these additives, one kind or a mixture of two or more kinds at any ratio therebetween could be used, in an amount conventionally used in this field without any specific limitation.

As the metal corrosion inhibitor, there is exemplified one or more selected from triazole derivatives, thiazole derivatives and thiadiazole derivatives, specifically benzotriazole, benzothiazole, tolyl triazole, octyl triazole, 2-mercapto benzothiazole, 2,5-dimercapto-1,3,4-thiadiazole, 2-mercapto-5-hydrocarbyl-1,3,4-thiadiazole, 2-dimercapto-5-dithio-1,3,4-thiadiazole, N,N-dihexyl aminomethylene benzotriazole, 2-mercapto benzothiadiazole, more specifically T551 (Jinzhou Kangtai Lubricating Oil Additive Co.), T561 (Jinzhou Kangtai Lubricating Oil Additive Co.), or T706 (Jinzhou Kangtai Lubricating Oil Additive Co.).

As the rust inhibitor, there is exemplified imidazoles and/or alkenyl succinic acid esters, such as 4,5-dihydroimidazole, alkenyl imidazoline succinate, alkenyl succinic acid esters, specifically T746 (Jinzhou Kangtai Lubricating Oil Additive Co.), T703 (Jinzhou Kangtai Lubricating Oil Additive Co.), or T747 (Jinzhou Kangtai Lubricating Oil Additive Co.).

As the pour point reducing agent, there is exemplified one or more selected from poly-α-olefins, vinyl acetate copolymers, dialkyl fumarates wherein the alkyl has a carbon atom number of from 8 to 18, polyalkyl methacrylates, and alkyl naphthalenes, specifically T803 (Wuxi Nanfang petroleum additive company), or V385 (Infineum company).

As the anti-foaming agent, there is exemplified silicone anti-foaming agents, such as silicone oils or polydimethylsiloxanes.

The lubricating oil composition of this invention exhibits excellent viscosity control and low temperature performance, shear stability, cleansing performance at elevated temperatures and anti-wear performance, whereby meeting the requirements set by gasoline engine oils of the SL/GF-3, SM/GF-4, SN/GF-5 or greater specification, diesel engine oils of the CH-4, CI-4, CJ-4 or greater specification, methanol fuel engine oils, gas engine oils, marine cylinder oils, two-stroke engine oils, four-stroke motorcycle oils and or gear oils.

EXAMPLE

The present invention is further illustrated by using the following examples, but not limiting to same.

The following table lists chemicals to be used in Examples and Comparative Examples.

| Chemicals | Specification | | Supplier |
|---|---|---|---|
| o-cresol | CP | ≥98.0% | Sinopharm Chemical Reagent Co., Ltd. |
| polyisobutene | HR-PIB | Mn = 1000 | Jilin Chemical Group Fine Chemicals Co., Ltd. |
| diethylenetriamine | CP | ≥98.0% | Beijing chemical plant |
| triethylenetetramine | CP | ≥95.0% | Sinopharm Chemical Reagent Co., Ltd. |
| tetraethylenepentamine | CP | ≥90.0% | Sinopharm Chemical Reagent Co., Ltd. |
| formaldehyde | AR | $CH_2O$: 37.0-40.0% | Sinopharm Chemical Reagent Co., Ltd. |
| polyformaldehyde | AR | ≥94.0% | Sinopharm Chemical Reagent Co., Ltd. |
| boron trifluoride•diethyl ether | CP | $BF_3$: 47.0-47.7% | Sinopharm Chemical Reagent Co., Ltd. |
| Butanol | CP | ≥98.0 | Sinopharm Chemical Reagent Co., Ltd. |
| toluene | | ≥99.7 | Beijing chemical plant |
| xylene | AR | ≥99.0% | Beijing chemical plant |
| 4-tert-amyl phenol | | 99% | Alfa aesar (Tianjing) Chemical Co., Ltd. |
| 4-nonyl phenol | | | Tokyo Kasei kogyo Co. |
| 4-dodecyl phenol | | | Tokyo Kasei kogyo. Co |

Example 1

To a 500 ml four necked flask equipped with a stirrer, a thermometer, a condensing tube and a dropping funnel, there were added 34.93 g (0.323 mol) o-cresol, 6.88 g (0.048 mol) boron trifluoride•diethyl ether (as the alkylating catalyst), 100 ml n-hexane as the solvent and 161.61 g (0.162 mol) polyisobutene, at 80 degrees Celsius to react for 2 h. Upon completion of the reaction, the reaction mixture was washed once with a 5 wt % KOH aqueous solution, and then washed with hot water till neutral to remove any catalyst, and then vacuum distillated to remove any solvent and unreacted o-cresol, to obtain a polyisobutenyl o-cresol, having a hydroxyl value of 53.49 mgKOH/g. The hydroxyl value was determined by referring to the acetic anhydride method in GB/T7383-2007.

The reaction procedure can be illustrated as follows.

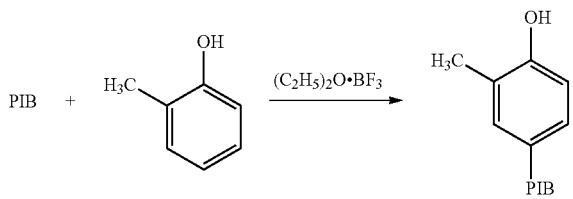

Figure 1:
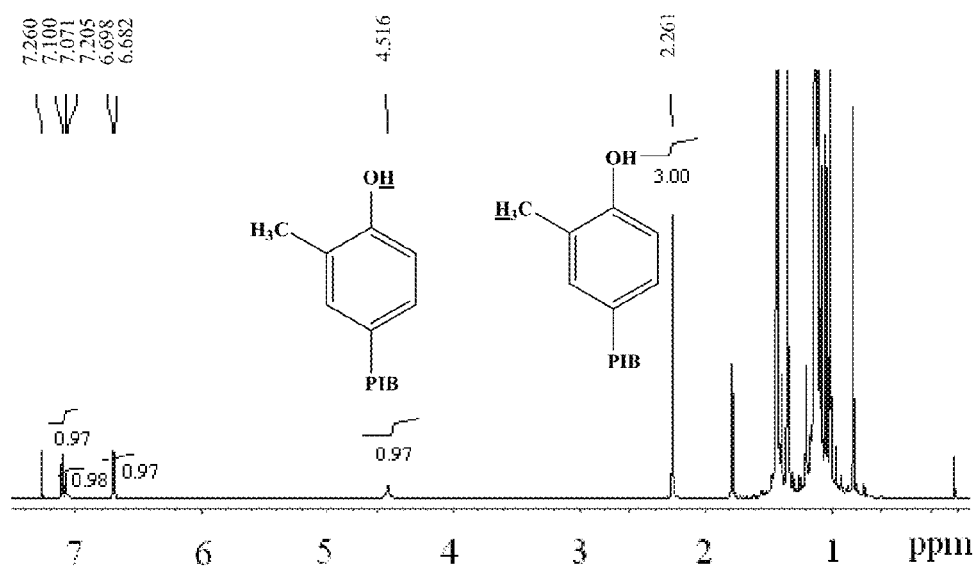
FIG. 1 illustrates the 1H NMR spectrum of the polyisobutenyl o-cresol produced in Example 1.
Figure 2:
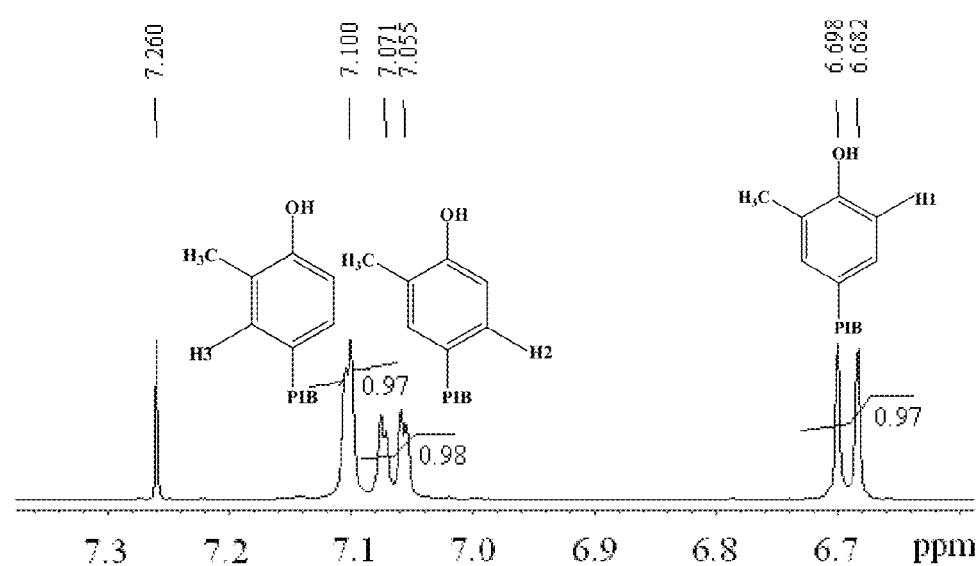
FIG. 2 illustrates the benzene ring region in the 1H NMR spectrum of the polyisobutenyl o-cresol produced in Example 1.

FIG. 1 illustrates the 1H NMR spectrum of the polyisobutenyl o-cresol produced in Example 1. FIG. 2 illustrates the benzene ring region in the 1H NMR spectrum of the polyisobutenyl o-cresol produced in Example 1. On the basis of FIGS. 1 and 2, it can be seen that: the peak at the chemical shift of 2.261 was identified as the characteristic peak of the hydrogen of methyl on the benzene ring of the polyisobutenyl o-cresol; the peak at the chemical shift of 4.516 was identified as the characteristic peak of the hydrogen of the hydroxyl on the benzene ring of the polyisobutenyl o-cresol; the double peak at the chemical shift of 6.69 was identified as the characteristic peak of the hydrogen H1; the double peak at the chemical shift of 7.06 was identified as the characteristic peak of the hydrogen H2; the single peak at the chemical shift of 7.10 was identified as the characteristic peak of the hydrogen H3. If the integral of the hydrogen of methyl is defined as 3, the value of the integral ratio between the hydrogen on the benzene ring, the hydrogen of the hydroxyl and the hydrogen of methyl was calculated as 0.97:0.98:0.97:0.97:3.00, approximating to the theoretical value of 1:1:1:1:3. As can be seen from this NMR spectra analysis, the p-polyisobutenyl o-cresol was obtained as anticipated.

Example 2

Under the protective atmosphere of nitrogen gas, 47.16 g (0.045 mol) of the polyisobutenyl o-cresol produced in Example 1 was added to a 500 ml four necked flask equipped with a stirrer, a thermometer and a liquid separator, and then there were added 2.70 g (0.045 mol) ethylene diamine, 3.83 g (0.047 mol) formaldehyde, and there was added 47 ml toluene as the solvent, after reacted at 80 degrees Celsius for 1.5 h, cooled to the room temperature, there were added 4.97 g (0.0225 mol) 4-nonyl phenol, 3.83 g (0.047 mol) formaldehyde, reacted at 70 degrees Celsius for 1 h. Upon completion of the reaction, the reaction mixture was vacuum distillated to remove the solvent and any water produced, to obtain the final Mannich base.

The reaction procedure can be illustrated as follows.

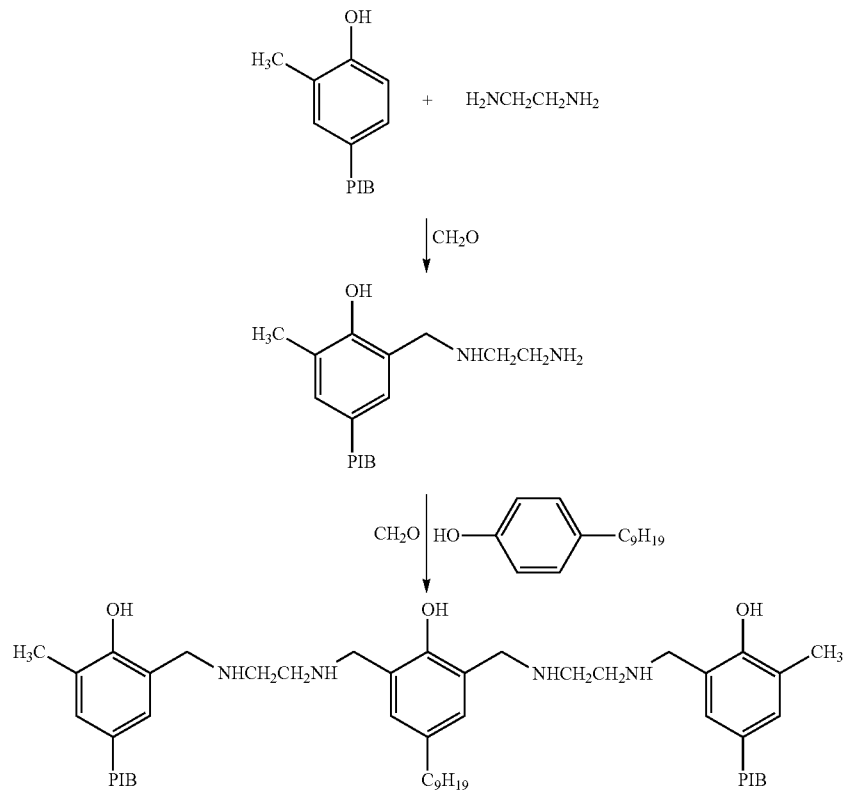

FIG. 3 compares the 1H NMR spectrum of the Mannich base produced in Example 2 with that of the polyisobutenyl o-cresol produced in Example 1.

FIG. 4 compares the benzene ring region in the 1H NMR spectrum of the Mannich base produced in Example 2 and that of the polyisobutenyl o-cresol produced in Example 1. On the basis of FIGS. 3 and 4, it can be seen that: the peak at the chemical shift of 3.7 was identified as the characteristic peak of the hydrogen of methylene resulted from the carbonyl of formaldehyde; the peak at the chemical shift of 2.45 was identified as the characteristic peak of the hydrogen of the two methylene groups on ethylenediamine. Further, upon comparison between Example 2 and Example 1, it can be seen that: the hydrogen at the ortho position to the hydroxyl on the benzene ring of the polyisobutenyl o-cresol was consumed by the Mannich reaction, as a result, the characteristic peak of hydrogen in the benzene ring region was reduced from 3 to 2 in number. As can be seen from this NMR spectra analysis, the polyisobutenyl o-cresol was obtained as anticipated.

FIG. 5 illustrates the GPC spectrum of the polyisobutenyl o-cresol produced in Example 1. FIG. 6 illustrates the GPC spectrum of the Mannich base produced in Example 2. As can be seen from FIG. 5 and FIG. 6, by doubling the starting materials for the Mannich reaction, the molecular weight of the produced Mannich base was increased accordingly, which indicates that the Mannich base had been obtained as anticipated.

Example 3

Under the protective atmosphere of nitrogen gas, 44.92 g (0.043 mol) of the polyisobutenyl o-cresol produced in Example 1 was added to a 500 ml four necked flask equipped with a stirrer, a thermometer and a liquid separator, and then there were added 4.64 g (0.043 mol) diethylenetriamine, 3.65 g (0.045 mol) formaldehyde, and there was added 47 ml xylene as the solvent, at 90 degrees Celsius to react for 1.5 h, and then cooled to the room temperature, there were added 5.64 g (0.0215 mol) 4-dodecyl phenol, 3.65 g (0.045 mol) formaldehyde, reacted at 70 degrees Celsius for 1 h. Upon completion of the reaction, the reaction mixture was vacuum distillated to remove the solvent and any water produced, to obtain the final Mannich base.

Example 4

Under the protective atmosphere of nitrogen gas, 53.37 g (0.051 mol) of the polyisobutenyl o-cresol produced in Example 1 was added to a 500 ml four necked flask equipped with a stirrer, a thermometer and a liquid separator, and then there were added 7.46 g (0.051 mol) triethylenetetramine, 4.38 g (0.054 mol) formaldehyde, and there was added 54 ml xylene as the solvent, at 100 degrees Celsius to react for 1.5 h, and then cooled to the room temperature, there were added 2.76 g (0.0255 mol) p-cresol, 4.38 g (0.054 mol) formaldehyde, reacted at 80 degrees Celsius for 1 h. Upon completion of the reaction, the reaction mixture was vacuum distillated to remove the solvent and any water produced, to obtain the final Mannich base.

Example 5

Under the protective atmosphere of nitrogen gas, 58.80 g (0.056 mol) of the polyisobutenyl o-cresol produced in Example 1 was added to a 500 ml four necked flask equipped with a stirrer, a thermometer and a liquid separator, and then there were added 2.89 g (0.028 mol) diethylenetriamine, 4.78 g (0.059 mol) formaldehyde, and there was added 53 ml toluene as the solvent, at 100 degrees Celsius to react for 1.5 h, then cooled to the room temperature, there were added 1.51 g (0.014 mol) p-cresol, 2.39 g (0.029 mol) formaldehyde, reacted at 80 degrees Celsius for 1 h. Upon completion of the reaction, the reaction mixture was vacuum distillated to remove the solvent and any water produced, to obtain the final Mannich base.

The reaction procedure can be illustrated as follows.

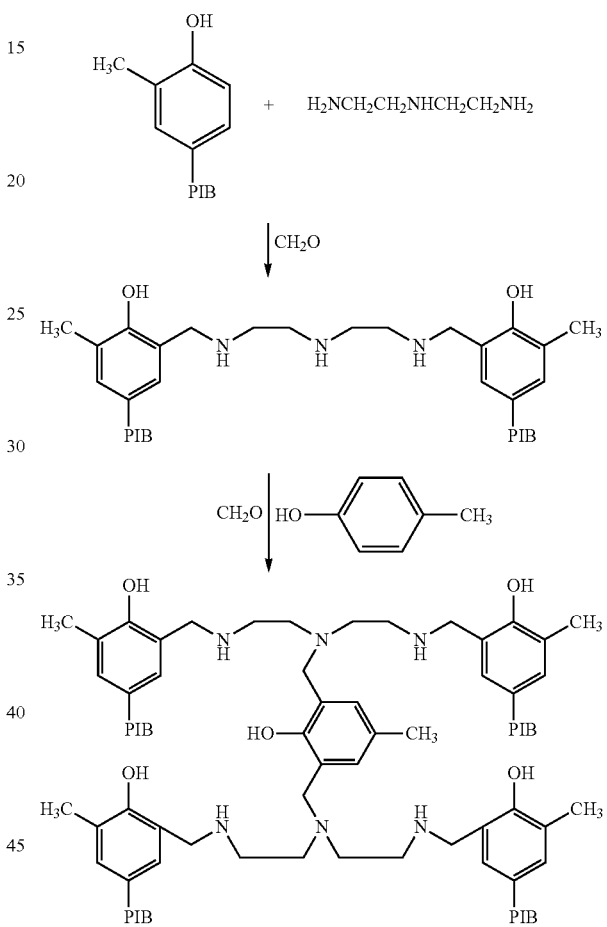

FIG. 7 illustrates the GPC spectrum of the Mannich base produced in Example 5. As can be seen from these FIG. 5, FIG. 6 and FIG. 7, by doubling the starting materials for the Mannich reaction, the molecular weight of the produced Mannich base was increased accordingly, which indicates that the Mannich base had been obtained as anticipated.

Example 6

Under the protective atmosphere of nitrogen gas, 40.01 g (0.038 mol) of the polyisobutenyl o-cresol produced in Example 1 was added to a 500 ml four necked flask equipped with a stirrer, a thermometer and a liquid separator, and then there were added 3.61 g (0.019 mol) tetraethylenepentamine, 3.25 g (0.040 mol) formaldehyde, was added 38 ml xylene as the solvent, after reacted at 80 degrees Celsius for 1.5 h, cooled to the room temperature, there were added 2.10 g (0.0095 mol) 4-nonyl phenol, 1.63 g (0.020 mol) formaldehyde, reacted at 70 degrees Celsius for 1 h. Upon completion of the reaction, the reaction mixture was vacuum distillated to remove the solvent and any water produced, to obtain the final Mannich base.

Example 7

Under the protective atmosphere of nitrogen gas, 51.33 g (0.049 mol) of the polyisobutenyl o-cresol produced in Example 1 was added to a 500 ml four necked flask equipped with a stirrer, a thermometer and a liquid separator, and then there were added 3.58 g (0.024 mol) triethylenetetramine, 1.53 g (0.051 mol) polyformaldehyde, and there was added 48 ml toluene as the solvent, after reacted at 90 degrees Celsius for 1.5 h, cooled to the room temperature, there were added 3.15 g (0.012 mol) 4-dodecyl phenol, 0.78 g (0.026 mol) polyformaldehyde, reacted at 70 degrees Celsius for 1 h. Upon completion of the reaction, the reaction mixture was vacuum distillated to remove the solvent and any water produced, to obtain the final Mannich base.

Example 8

Under the protective atmosphere of nitrogen gas, 2.86 g (0.048 mol) ethylenediamine and 6.24 g (0.024 mol) 4-dodecyl phenol were added to a 500 ml four necked flask equipped with a stirrer, a thermometer and a liquid separator, and then there was added 49 ml xylene as the solvent, at 50 degrees Celsius there was added 3.86 g (0.048 mol) formaldehyde solution and reacted for 0.5 h, and then heated to 110 degrees Celsius, further reacted for 2.5 h, cooled to 50 degrees Celsius, there was added 45.11 g (0.043 mol) of the polyisobutenyl o-cresol produced in Example 1, upon complete dissolution of the polyisobutenyl o-cresol, there was added 3.40 g (0.043 mol) formaldehyde solution, heated to 120 degrees Celsius, further reacted for 2 h. Upon completion of the reaction, the reaction mixture was vacuum distillated to remove the solvent and any water produced, to obtain the final Mannich base.

Example 9

Under the protective atmosphere of nitrogen gas, 5.70 g (0.039 mol) triethylenetetramine and 1.95 g (0.018 mol) p-cresol were added to a 500 ml four necked flask equipped with a stirrer, a thermometer and a liquid separator, and then there was added 49 ml xylene as the solvent, at 80 degrees Celsius there was added 1.41 g (0.047 mol) polyformaldehyde, gradually heated to 120 degrees Celsius and reacted for 2.5 h, and then there was added 40.91 g (0.039 mol) of the polyisobutenyl o-cresol produced in Example 1, after completely dissolved, there was added 1.20 g (0.040 mol) polyformaldehyde, further reacted for 2 h. Upon completion of the reaction, the reaction mixture was vacuum distillated to remove the solvent and any water produced, to obtain the final Mannich base.

Example 10

Under the protective atmosphere of nitrogen gas, 39.86 g (0.038 mol) of the polyisobutenyl o-cresol produced in Example 1, 2.46 g (0.041 mol) ethylenediamine, 3.06 g (0.019 mol) 4-tert-amyl phenol were added to a 500 ml four necked flask equipped with a stirrer, a thermometer and a liquid separator, and there was added 44 ml xylene as the solvent, heated to 80 degrees Celsius and stirred till a homogeneous reaction system was obtained, then there were added 3.18 g (0.106 mol) polyformaldehyde, and gradually heated to 130 degrees Celsius, reacted at this temperature for 4 h. Upon completion of the reaction, the reaction mixture was vacuum distillated to remove the solvent and any water produced, to obtain the final Mannich base.

Example 11

Under the protective atmosphere of nitrogen gas, 45.11 g (0.043 mol) of the polyisobutenyl o-cresol produced in Example 1, 4.16 g (0.022 mol) tetraethylenepentamine, 2.42 g (0.011 mol) 4-nonyl phenol were added to a 500 ml four necked flask equipped with a stirrer, a thermometer and a liquid separator, and there was added 50 ml toluene as the solvent, stirred till a homogeneous reaction system was obtained, heated to 45-50 degrees Celsius, and there was dropwise added 5.92 g (0.073 mol) formaldehyde solution over a period of 0.5 h, and after completion of this dropwise addition, further reacted for 0.5 h, and then gradually heated to 110 degrees Celsius, further reacted for 4 h. Upon completion of the reaction, the reaction mixture was vacuum distillated to remove the solvent and any water produced, to obtain the final Mannich base.

Comparative Example 1

Under the protective atmosphere of nitrogen gas, 51.27 g (0.049 mol) of the polyisobutenyl o-cresol produced in Example 1 was added to a 500 ml four necked flask equipped with a stirrer, a thermometer and a liquid separator, and then there were added 9.28 g (0.049 mol) tetraethylenepentamine, 4.77 g (0.059 mol) formaldehyde, and there was added 37 ml xylene as the solvent, at 80 degrees Celsius reacted for 1.5 h. Upon completion of the reaction, the reaction mixture was vacuum distillated to remove the solvent and any water produced, to obtain the final Mannich base.

Comparative Example 2

Under the protective atmosphere of nitrogen gas, 48.27 g (0.046 mol) of the polyisobutenyl o-cresol produced in Example 1 was added to a 500 ml four necked flask equipped with a stirrer, a thermometer and a liquid separator, and then there were added 3.36 g (0.023 mol) triethylenetetramine, 4.46 g (0.055 mol) formaldehyde, and there was added 45 ml toluene as the solvent, heated and stirred until homogeneous, and then there was dropwise added 4.46 g (0.055 mol) formaldehyde, at 80 degrees Celsius reacted for 1.5 h. Upon completion of the reaction, the reaction mixture was vacuum distillated to remove the solvent and any water produced, to obtain the final Mannich base.

Examples 12-21 and Comparative Examples 3-6

The formulation of each of the lubricating oil compositions for gasoline engine of Examples 12-21 and Comparative Examples 3-6 was listed in Table 1. In each case, each component in this table was added to a blending container at the predetermined ratio, and mixed together at 50 degrees Celsius under stirring for 2 h, to obtain a lubricating oil composition for gasoline engine of the SN 5W-30 specification.

The lubricating oil composition produced in each Example and Comparative Example was taken as the test sample to conduct the engine crankcase coking simulation test, which simulates depositing on the piston. During this test, 300 ml of the test sample was added to a coke-forming plate simulator, heated up to 150 degrees Celsius, continuously splashed onto an aluminium plate having a temperature of 310 degrees Celsius. After 6 hours, coke deposited on the aluminium plate was weighted, expressed as the deposit amount (unit: mg). The more the deposit amount is, the worse the piston cleansing performance of the test sample exhibits. The results were listed in Table 1.

TABLE 1

| Component amount, wt % | Example 12 | Example 13 | Example 14 | Example 15 | Example 16 | Example 17 | Example 18 |
|---|---|---|---|---|---|---|---|
| Example 2 | 3.5 | | | | | | |
| Example 3 | | 3.5 | | | | | |
| Example 4 | | | 2.5 | | | | |
| Example 5 | | | | 2.5 | | | |
| Example 6 | | | | | 4.0 | | |
| Example 7 | | | | | | 3.5 | |
| Example 8 | | | | | | | 2.5 |
| Example 9 | | | | | | | |
| Example 10 | | | | | | | |
| Example 11 | | | | | | | |
| Comparative Example 1 | | | | | | | |
| Comparative Example 2 | | | | | | | |
| butyl octyl diphenylamine | 0.2 | 0.2 | 0.2 | 0.2 | 0.2 | 0.2 | 0.5 |
| 2,2-methylene bis (4-methyl-6-tert-butyl phenol) | 0.2 | 0.2 | 0.2 | 0.2 | 0.2 | 0.2 | 0.1 |
| pentaerythritol polyisobutylene succinic acid (with PIB having a number-averaged molecular weight Mn of 1300) | | | | | | | |
| high alkali value calcium sulfonate (TBN 300) | 0.5 | 0.5 | 0.5 | 0.5 | 0.5 | 0.5 | 0.5 |
| low alkali value calcium sulfonate (TBN 40) | 0.3 | 0.3 | 0.3 | 0.3 | 0.3 | 0.3 | 0.3 |
| zinc n-butyl n-octyl dithiophosphate | 0.7 | 0.7 | 0.7 | 0.7 | 0.7 | 0.9 | 0.7 |
| molybdenyl dialkyl dithiophosphate, Molyvan 822 | 0.05 | 0.05 | 0.05 | 0.05 | 0.05 | 0.1 | 0.05 |
| oleamide | 0.3 | 0.3 | 0.3 | 0.3 | 0.3 | 0.3 | 0.3 |
| Group II base oil 100N (with a viscosity index of 115) | 42 | 42 | 42 | 42 | 42 | 42 | 42 |
| Group II base oil 150N (with a viscosity index of 109) | remaining | remaining | remaining | remaining | remaining | remaining | remaining |
| Deposit amount/mg | 6.9 | 7.2 | 7.6 | 8.4 | 4.3 | 5.7 | 8.3 |

| Component amount, wt % | Example 19 | Example 20 | Example 21 | Comparative Example 3 | Comparative Example 4 | Comparative Example 5 | Comparative Example 6 |
|---|---|---|---|---|---|---|---|
| Example 2 | | | | | | | |
| Example 3 | | | | | | | |
| Example 4 | | | | | | | |
| Example 5 | | | | | | | |
| Example 6 | | | | | | | |
| Example 7 | | | | | | | |
| Example 8 | | | | | | | |
| Example 9 | 3.0 | | | | | | |
| Example 10 | | 4.5 | | | | | |
| Example 11 | | | 4.0 | | | | |
| Comparative Example 1 | | | | 2.5 | | | |
| Comparative Example 2 | | | | | 2.5 | | |
| butyl octyl diphenylamine | 0.2 | 0.2 | 0.2 | 0.2 | 0.2 | 0.2 | 0.2 |
| 2,2-methylene bis (4-methyl-6-tert-butyl phenol) | 0.2 | 0.2 | 0.2 | 0.2 | 0.2 | 0.2 | 0.2 |
| pentaerythritol polyisobutylene succinic acid (with PIB having a number-averaged molecular weight Mn of 1300) | | | | | | 2.5 | 3.5 |
| high alkali value calcium sulfonate (TBN 300) | 0.5 | 0.5 | 0.5 | 0.5 | 0.5 | 2.5 | 1.5 |
| low alkali value calcium sulfonate (TBN 40) | 0.3 | 0.8 | 0.3 | 0.3 | 0.3 | 0.3 | 0.3 |
| zinc n-butyl n-octyl dithiophosphate | 0.7 | 0.7 | 0.7 | 0.7 | 0.7 | 0.7 | 0.7 |
| molybdenyl dialkyl dithiophosphate, Molyvan 822 | 0.05 | 0.05 | 0.05 | 0.05 | 0.05 | 0.05 | 0.05 |

TABLE 1-continued

| | | | | | | | |
|---|---|---|---|---|---|---|---|
| oleamide | 0.3 | 0.3 | 0.6 | 0.3 | 0.3 | 0.3 | 0.3 |
| Group II base oil 100N (with a viscosity index of 115) | 42 | 42 | 42 | 42 | 42 | 42 | 42 |
| Group II base oil 150N (with a viscosity index of 109) | remaining | remaining | remaining | remaining | remaining | remaining | remaining |
| Deposit amount/mg | 5.6 | 4.1 | 4.7 | 9.5 | 10.2 | 14.6 | 11.8 |

Examples 22-31 and Comparative Examples 7-10

The formulation of each of the lubricating oil compositions for diesel engine of Examples 22-31 and Comparative Examples 7-10 was listed in Table 2. In each case, each component in this table was added to a blending container at the predetermined ratio, and mixed together at 50 degrees Celsius under stirring for 2 h, to obtain a lubricating oil composition for diesel engine of the CH-4 specification with a viscosity grade of 10W-40.

The lubricating oil composition produced in each Example and Comparative Example was taken as the test sample to conduct the engine crankcase coking simulation test, which simulates depositing on the piston. During this test, 300 ml of the test sample was added to a coke-forming plate simulator, heated up to 100 degrees Celsius, continuously splashed onto an aluminium plate having a temperature of 330 degrees Celsius. After 5 hours, coke deposited on the aluminium plate was weighted, expressed as the deposit amount (unit: mg). The more the deposit amount is, the worse the piston cleansing performance of the test sample exhibits. The results were listed in Table 2.

TABLE 2

| Component amount, wt % | Example 22 | Example 23 | Example 24 | Example 25 | Example 26 | Example 27 | Example 28 |
|---|---|---|---|---|---|---|---|
| Example 2 | 6.5 | | | | | | |
| Example 3 | | 6.5 | | | | | |
| Example 4 | | | 7.5 | | | | |
| Example 5 | | | | 6.5 | | | |
| Example 6 | | | | | 6.5 | | |
| Example 7 | | | | | | 6.5 | |
| Example 8 | | | | | | | 6.5 |
| Example 9 | | | | | | | |
| Example 10 | | | | | | | |
| Example 11 | | | | | | | |
| Comparative Example 1 | | | | | | | |
| Comparative Example 2 | | | | | | | |
| butyl octyl diphenylamine | 0.2 | 0.2 | 0.2 | 0.2 | 0.2 | 0.2 | 0.2 |
| 2,2'-thio-bis [3-(3,5-di-tert-butyl-4-hydroxyphenyl) propionate ethyl] | 0.2 | 0.2 | 0.2 | 0.2 | 0.2 | 0.2 | 0.2 |
| polyisobutylene succinimide (with PIB having a number-averaged molecular weight Mn of 1000) | 1.5 | 1.5 | 1.5 | 1.5 | 1.5 | 1.5 | 1.5 |
| borated polyisobutylene succinimide (with PIB having a number-averaged molecular weight Mn of 2300 and a boron content of 0.35%) | | | | | | | |
| high alkali value magnesium sulfonate (TBN 400) | 0.5 | 0.5 | 0.5 | 0.5 | 0.5 | 0.5 | 0.5 |
| high alkali value calcium sulfurized alkyl phenate (TBN 250) | 0.4 | 0.4 | 0.4 | 0.4 | 0.4 | 0.4 | 0.4 |
| medium alkali value calcium sulfurized alkyl phenate (TBN 150) | 1.2 | 1.2 | 1.2 | 1.2 | 1.2 | 1.2 | 1.2 |
| zinc diiso-octyl dithiophosphate | 0.7 | 0.7 | 0.7 | 0.7 | 0.7 | 0.7 | 0.7 |
| zinc iso-propyl iso-hexyl dithiophosphate | 0.9 | 0.05 | 0.05 | 0.05 | 0.05 | 0.05 | 0.05 |
| glyceryl monooleate | 0.3 | 0.3 | 0.3 | 0.3 | 0.3 | 0.3 | 0.3 |
| Group II base oil 100N (with a viscosity index of 115) | 42 | 42 | 42 | 42 | 42 | 42 | 42 |
| Group II base oil 150N (with a viscosity index of 109) | remaining | remaining | remaining | remaining | remaining | remaining | remaining |
| Deposit amount/mg | 7.5 | 8.0 | 5.8 | 6.4 | 7.6 | 8.4 | 7.3 |

| Component amount, wt % | Example 29 | Example 30 | Example 31 | Comparative Example 7 | Comparative Example 8 | Comparative Example 9 | Comparative Example 10 |
|---|---|---|---|---|---|---|---|
| Example 2 | | | | | | | |
| Example 3 | | | | | | | |
| Example 4 | | | | | | | |
| Example 5 | | | | | | | |
| Example 6 | | | | | | | |
| Example 7 | | | | | | | |
| Example 8 | | | | | | | |
| Example 9 | 5.0 | | | | | | |

TABLE 2-continued

| Component | C1 | C2 | C3 | C4 | C5 | C6 | C7 |
|---|---|---|---|---|---|---|---|
| Example 10 | | 6.2 | | | | | |
| Example 11 | 7.0 | | | | | | |
| Comparative Example 1 | | | 6.5 | | | | |
| Comparative Example 2 | | | | 6.5 | | | |
| butyl octyl diphenylamine | 0.2 | 0.2 | 0.2 | 0.2 | 0.2 | 0.2 | 0.2 |
| 2,2'-thio-bis [3-(3,5-di-tert-butyl-4-hydroxyphenyl) propionate ethyl] | 0.2 | 0.2 | 0.2 | 0.2 | 0.2 | 0.2 | 0.2 |
| polyisobutylene succinimide (with PIB having a number-averaged molecular weight Mn of 1000) | 1.5 | 1.5 | 1.5 | 1.5 | 1.5 | 1.5 | 1.5 |
| borated polyisobutylene succinimide (with PIB having a number-averaged molecular weight Mn of 2300 and a boron content of 0.35%) | | | | | | 6.5 | 7.5 |
| high alkali value magnesium sulfonate (TBN 400) | 0.5 | 0.5 | 0.5 | 0.5 | 0.5 | 2.5 | 1.5 |
| high alkali value calcium sulfurized alkyl phenate (TBN 250) | 0.4 | 0.4 | 0.4 | 0.4 | 0.4 | 0.4 | 1.4 |
| medium alkali value calcium sulfurized alkyl phenate (TBN 150) | 1.2 | 1.2 | 1.2 | 1.2 | 1.2 | 1.2 | 1.2 |
| zinc diiso-octyl dithiophosphate | 0.7 | 0.7 | 0.7 | 0.7 | 0.7 | 0.7 | 0.7 |
| zinc iso-propyl iso-hexyl dithiophosphate | 0.05 | 0.05 | 0.05 | 0.05 | 0.05 | 0.05 | 0.05 |
| glyceryl monooleate | 0.3 | 0.3 | 0.3 | 0.3 | 0.3 | 0.3 | 0.3 |
| Group II base oil 100N (with a viscosity index of 115) | 42 | 42 | 42 | 42 | 42 | 42 | 42 |
| Group II base oil 150N (with a viscosity index of 109) | remaining | remaining | remaining | remaining | remaining | remaining | remaining |
| Deposit amount/mg | 8.7 | 7.5 | 7.2 | 10.3 | 11.2 | 13.8 | 12.6 |

Examples 32-41 and Comparative Examples 11-14

The formulation of each of the lubricating oil compositions for gas engine of Examples 32-41 and Comparative Examples 11-14 was listed in Table 3. In each case, each component in this table was added to a blending container at the predetermined ratio, and mixed together under stirring at 45 degrees Celsius at the normal pressure under stirring for 2 h, to obtain a lubricating oil composition for gas engine with a viscosity grade of SN 5W-40.

The lubricating oil composition produced in each Example and Comparative Example was taken as the test sample to conduct the engine crankcase coking simulation test, which simulates depositing on the piston. During this test, 300 ml of the test sample was added to a coke-forming plate simulator, heated•up to 140 degrees Celsius, continuously splashed onto an aluminium plate having a temperature of 320 degrees Celsius. After 6 hours, coke deposited on the aluminium plate was weighted, expressed as the deposit amount (unit: mg). The more the deposit amount is, the worse the piston cleansing performance of the test sample exhibits. The results were listed in Table 3.

TABLE 3

| Component amount, wt % | Example 32 | Example 33 | Example 34 | Example 35 | Example 36 | Example 37 | Example 38 |
|---|---|---|---|---|---|---|---|
| Example 2 | 1.6 | | | | | | |
| Example 3 | | 2.0 | | | | | |
| Example 4 | | | 0.8 | | | | |
| Example 5 | | | | 1.6 | | | |
| Example 6 | | | | | 1.6 | | |
| Example 7 | | | | | | 2.0 | |
| Example 8 | | | | | | | 1.5 |
| Example 9 | | | | | | | |
| Example 10 | | | | | | | |
| Example 11 | | | | | | | |
| Comparative Example 1 | | | | | | | |
| Comparative Example 2 | | | | | | | |
| 2,6-ditert-butyl-α-dimethylamino p-cresol | 0.4 | 0.4 | 0.4 | 0.4 | 0.4 | 0.4 | 0.7 |
| polyisobutylene succinimide (with PIB having a number-averaged molecular weight Mn of 1000) | | | | | | | |
| calcium salicylate (TBN 150) | 0.5 | 0.5 | 0.5 | 0.5 | 0.5 | 0.5 | 0.5 |
| low alkali value calcium sulfurized alkyl phenate (TBN 50) | 0.4 | 0.4 | 0.4 | 0.4 | 0.4 | 0.4 | 0.4 |
| zinc butyl 2-ethylhexyl dithiophosphate | 1.1 | 1.1 | 1.1 | 1.1 | 1.1 | 1.1 | 1.1 |
| monoester of oleic acid and triethanolamine | 0.3 | 0.3 | 0.3 | 0.3 | 0.3 | 0.3 | 0.3 |
| 2,5-dimercapto-1,3,4-thiadiazole | 0.05 | 0.05 | 0.05 | 0.05 | 0.05 | 0.05 | 0.05 |
| PAO8 base oil | 40 | 40 | 40 | 40 | 40 | 40 | 40 |

TABLE 3-continued

| Component amount, wt % | | | | Example 39 | Example 40 | Example 41 | Comparative Example 11 | Comparative Example 12 | Comparative Example 13 | Comparative Example 14 |
|---|---|---|---|---|---|---|---|---|---|---|
| PAO4 base oil | | | | remaining | remaining | remaining | remaining | remaining | remaining | remaining |
| Deposit amount/mg | | | | 11.7 | 10.9 | 12.4 | 11.3 | 12.5 | 12.1 | 12.8 |
| Example 2 | | | | | | | | | | |
| Example 3 | | | | | | | | | | |
| Example 4 | | | | | | | | | | |
| Example 5 | | | | | | | | | | |
| Example 6 | | | | | | | | | | |
| Example 7 | | | | | | | | | | |
| Example 8 | | | | | | | | | | |
| Example 9 | | | | 1.5 | | | | | | |
| Example 10 | | | | | 2.0 | | | | | |
| Example 11 | | | | | | 2.0 | | | | |
| Comparative Example 1 | | | | | | | 1.6 | | | |
| Comparative Example 2 | | | | | | | | 1.6 | | |
| 2,6-ditert-butyl-α-dimethylamino p-cresol | | | | 0.4 | 0.4 | 0.4 | 0.4 | 0.4 | 0.4 | 0.4 |
| polyisobutylene succinimide (with PIB having a number-averaged molecular weight Mn of 1000) | | | | | | | | | 2.0 | 1.6 |
| calcium salicylate (TBN 150) | | | | 0.5 | 0.5 | 0.2 | 0.5 | 0.5 | 1.5 | 0.5 |
| low alkali value calcium sulfurized alkyl phenate (TBN 50) | | | | 0.4 | 0.4 | 0.8 | 0.4 | 0.4 | 0.4 | 1.4 |
| zinc butyl 2-ethylhexyl dithiophosphate | | | | 1.1 | 1.3 | 1.1 | 1.1 | 1.1 | 1.1 | 1.1 |
| monoester of oleic acid and triethanolamine | | | | 0.5 | 0.3 | 0.3 | 0.3 | 0.3 | 0.3 | 0.3 |
| 2,5-dimercapto-1,3,4-thiadiazole | | | | 0.2 | 0.05 | 0.05 | 0.05 | 0.05 | 0.05 | 0.05 |
| PAO8 base oil | | | | 40 | 40 | 40 | 40 | 40 | 40 | 40 |
| PAO4 base oil | | | | remaining | remaining | remaining | remaining | remaining | remaining | remaining |
| Deposit amount/mg | | | | 11.9 | 10.1 | 10.5 | 13.9 | 14.2 | 16.5 | 17.7 |

The lubricating oil composition produced in each Example and Comparative Example was taken as the test sample to conduct the ball rust test (BRT). Throughout the bench scale test lasting for 18 hours, a metal ball protected by the test sample was made to continuously contact an acid liquid and air, with an acid liquid injection speed of 0.19 ml/h, an air flow rate of 40 ml/min and an oil temperature of 48 degrees Celsius. Upon completion of the test, the spherical reflection intensity of the metal ball was determined to obtain a gray value, which was used to determine the corrosion area, whereby scoring the anticorrosion performance of the test sample. The acid liquid was an acetic acid/HBr/hydrochloric acid/deionized water solution. The greater the score is, the better the anticorrosion performance is. The results were shown in Table 4. As revealed by the results, the lubricating oil composition of this invention exhibits excellent anticorrosion performance.

TABLE 4

| Lubricating oil composition | BRT score |
|---|---|
| Example 12 | 134 |
| Example 13 | 137 |
| Example 14 | 127 |
| Example 15 | 126 |
| Example 16 | 135 |
| Example 17 | 129 |
| Example 18 | 125 |
| Example 19 | 130 |
| Example 20 | 134 |
| Example 21 | 135 |
| Comparative Example 3 | 115 |
| Comparative Example 4 | 110 |
| Comparative Example 5 | 108 |
| Comparative Example 6 | 105 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A lubricating oil composition, comprising a Mannich base and a lubricant base oil, wherein the Mannich base comprises the structure unit (I) and the structure unit (II),

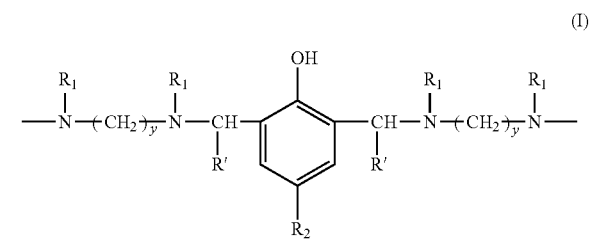

(I)

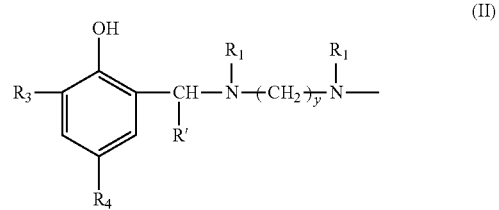

(II)

wherein, multiple $R_1$ may be the same as or different from one another, each independently selected from the group consisting of hydrogen, a $C_{1-4}$ linear or branched alkyl and a single bond; multiple R' may be the same as or different from one another, each independently selected from the group consisting of hydrogen and a $C_{1-6}$ linear or branched alkyl; $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5.

2. The lubricating oil composition according to claim 1, wherein the Mannich base is represented by the following formula (III):

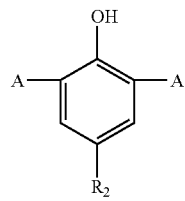
(III)

wherein, multiple A may be the same as or different from one another, each independently selected from the group consisting of

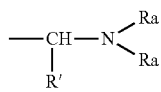

and hydrogen, with the proviso that at least one A represents

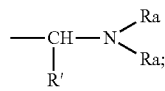

multiple R' may be the same as or different from one another, each independently selected from the group consisting of hydrogen and a $C_{1-6}$ linear or branched alkyl; multiple $R_a$ may be the same as or different from one another, each independently selected from the group consisting of hydrogen, a $C_{1-4}$ linear or branched alkyl and, with the proviso that at least one $R_a$ represents

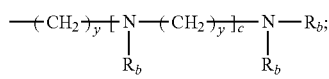

multiple $R_b$ may be the same as or different from one another, each independently selected from the group consisting of hydrogen,

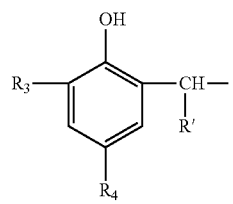

and a $C_{1-4}$ linear or branched alkyl, with the proviso that at least one $R_b$ represents

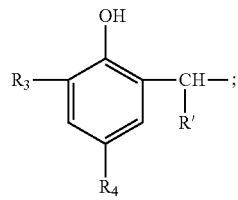

$R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple y may be the same as or different from one another, each independently selected from an integer of from 2 to 5; multiple c may be the same as or different from one another, each independently selected from an integer of from 0 to 10.

3. The lubricating oil composition according to claim 1, wherein the Mannich base is produced by a process comprising the step of reacting a phenolic compound of the formula (V), a phenolic compound of the formula (VI), a polyalkylenepolyamine of the formula (VII) and a $C_1$-$C_7$ linear or branched saturated aliphatic aldehyde to conduct a Mannich reaction,

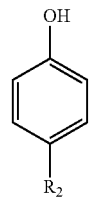
(V)

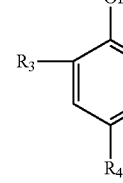
(VI)

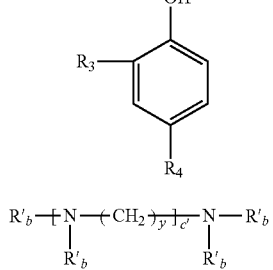
(VII)

wherein, $R_2$ represents a $C_{1-12}$ linear or branched alkyl; $R_3$ represents a $C_{1-6}$ linear or branched alkyl; $R_4$ represents a hydrocarbyl having a number-averaged molecular weight Mn of 300-3000; multiple $R_b'$ may be the same as or different from one another, each independently selected from the group consisting of hydrogen and a $C_{1-4}$ linear or branched alkyl, with the proviso that at least two of $R_b'$ are hydrogen; y represents an integer of from 2 to 5; c' represents an integer of from 1 to 11.

4. The lubricating oil composition according to claim 3, wherein the process is conducted in line with any one of the following ways:

Way (1) comprising the following steps:
the first step: reacting the phenolic compound of the formula (VI), the polyalkylenepolyamine of the formula (VII) and the $C_1$-$C_7$ linear or branched saturated aliphatic aldehyde at a reaction temperature of 50 to 200 degrees Celsius to conduct a Mannich reaction, to produce an intermediate; and the second step: reacting the intermediate, the phenolic compound of the formula (V) and the $C_1$-$C_7$ linear or branched saturated aliphatic aldehyde at a reaction temperature of 40 to 200 degrees Celsius to conduct a Mannich reaction, so as to produce the Mannich base, or Way (2) comprising the following steps:

the first step: reacting the phenolic compound of the formula (V), the polyalkylenepolyamine of the formula (VII) and the $C_1$-$C_7$ linear or branched saturated aliphatic aldehyde at a reaction temperature of 40 to 200 degrees Celsius to conduct a Mannich reaction, to produce an intermediate; and the second step: reacting the intermediate, the phenolic compound of the formula (VI) and the $C_1$-$C_7$ linear or branched saturated aliphatic aldehyde at a reaction temperature of 50 to 200 degrees Celsius to conduct a Mannich reaction, so as to produce the Mannich base, or Way (3) comprising the step of reacting the phenolic compound of the formula (V), the phenolic compound of the formula (VI), the polyalkylenepolyamine of the formula (VII) and the $C_1$-$C_7$ linear or branched saturated aliphatic aldehyde at a reaction temperature of 40 to 200 degrees Celsius to conduct a Mannich reaction to produce the Mannich base.

5. The lubricating oil composition according to claim 4, wherein in the process, in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.3-3:0.3-3.5; in the second step of Way (1), the ratio by molar between the intermediate, the phenolic compound of the formula (V) and the $C_1$-$C_7$ linear or branched saturated aliphatic aldehyde is 1:0.2-1.5:0.2-2; in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.5-2.5:1.5-3; in the second step of Way (2), the ratio by molar between the intermediate, the phenolic compound of the formula (VI) and the $C_1$-$C_7$ linear or branched saturated aliphatic aldehyde is 1:1.5-3:1.5-3; in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1-5:1-3:2-8.

6. The lubricating oil composition according to claim 3, wherein in the process, the Mannich reaction is conducted in the presence of one or more diluent selected from the group consisting of polyolefins, mineral base oils and polyethers.

7. The lubricating oil composition according to claim 3, wherein in the process, the phenolic compound of the formula (VI) is produced by in the presence of an alkylating catalyst, reacting a phenolic compound of the formula (IV) with a polyolefin having a number-averaged molecular weight Mn of 300-3000 to conduct an alkylation reaction,

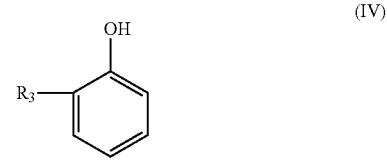

wherein, $R_3$ is as defined in claim 3.

8. The lubricating oil composition according to claim 1, further comprising one or more lubricating oil additives selected from the group consisting of antioxidants, dispersing agents, detergents, anti-wear agents and friction modifiers, wherein on a weight basis, the antioxidant accounts for 0-10 wt % of the total weight of the lubricating oil composition, the dispersing agent accounts for 0.5 to 15 wt % of the total weight of the lubricating oil composition, the detergent accounts for 0.2 to 20 wt % of the total weight of the lubricating oil composition, the anti-wear agent accounts for 0.1 to 10 wt % of the total weight of the lubricating oil composition, the friction modifier accounts for 0.01 to 5 wt % of the total weight of the lubricating oil composition.

9. The lubricating oil composition according to claim 8, wherein the antioxidant is one or more selected from the group consisting of amine antioxidants, phenol-ester antioxidants, thio phenol-ester antioxidants and phenolic antioxidants, the dispersing agent is one or more selected from the group consisting of polyisobutylene succinimide based dispersing agents, borated polyisobutylene succinimide based dispersing agents and succinic ester based dispersing agent, the detergent is one or more selected from the group consisting of sulfonate detergents, alkyl phenate detergents, sulfurized alkyl phenate detergents, salicylate detergents and naphthenate detergent, the anti-wear agent is one or more selected from the group consisting of dialkyl dithiophosphate anti-wear agents, phosphoric ester type extreme pressure anti-wear agents, sulfurized olefin based anti-wear agents, dialkyl dithiocarbamate anti-wear agents and thiadiazole derivative anti-wear agents, the friction modifier is one or more selected from the group consisting of oil-soluble organo-molybdenum friction modifiers, ashless friction modifiers, and organic boronic acid ester friction modifiers.

10. The lubricating oil composition according to claim 1, wherein on a weight basis, the Mannich base accounts for 0.01-20 wt % of the total weight of the lubricating oil composition.

11. A process for producing the lubricating oil composition according to claim 1, comprising the step of mixing the Mannich base and the lubricant base oil.

12. The lubricating oil composition according to claim 1, wherein the ratio by molar of the structure unit (I) and the structure unit (II) is 1:1 to 1:15.

13. The lubricating oil composition according to claim 2, wherein $R_2$ is a $C_{5-12}$ linear or branched alkyl; multiple c may be the same as or different from one another, each independently selected from an integer of from 2 to 5.

14. The lubricating oil composition according to claim 5, wherein in the process, in the first step of Way (1), the ratio by molar between the phenolic compound of the formula (VI), the polyalkylenepolyamine of the formula (VII) and the $C_1$-$C_7$ linear or branched saturated aliphatic aldehyde is 1:0.5-1.5:0.5-2; in the second step of Way (1), the ratio by molar between the intermediate, the phenolic compound of the formula (V) and the $C_1$-$C_7$ linear or branched saturated aliphatic aldehyde is 1:0.3-0.8:0.3-1.5; in the first step of Way (2), the ratio by molar between the phenolic compound of the formula (V), the polyalkylenepolyamine of the formula (VII) and the $C_1$-$C_7$ linear or branched saturated aliphatic aldehyde is 1:1.7-2.2:1.7-2.5; in the second step of Way (2), the ratio by molar between the intermediate, the phenolic compound of the formula (VI) and the $C_1$-$C_7$ linear or branched saturated aliphatic aldehyde is 1:1.7-2.3:1.7-2.5; in Way (3), the ratio by molar between the phenolic compound of the formula (V), the phenolic compound of the formula (VI), the polyalkylenepolyamine of the formula (VII) and the $C_1$-$C_7$ linear or branched saturated aliphatic aldehyde is 1:1.8-4.3:1.8-2.3:3.5-6.5.

* * * * *